United States Patent [19]

Hoeltje et al.

[11] Patent Number: 4,968,699
[45] Date of Patent: Nov. 6, 1990

[54] PYRIDO[1,2-A]INDOLES AND THEIR USE AS CNS AGENTS

[75] Inventors: Dagmar Hoeltje; Ljerka Jozic; Dietrich Thielke, all of Gronau, Fed. Rep. of Germany

[73] Assignee: Beecham-Wuelfing GmbH & Co., Fed. Rep. of Germany

[21] Appl. No.: 135,837

[22] Filed: Dec. 21, 1987

[30] Foreign Application Priority Data

Dec. 22, 1986 [GB] United Kingdom ............... 8630635
Sep. 5, 1987 [GB] United Kingdom ............... 8720946

[51] Int. Cl.[5] .................. A61K 31/395; C07D 451/00; C07D 417/00
[52] U.S. Cl. .................. 514/235.5; 514/212; 514/228.2; 514/252; 514/294; 540/597; 544/60; 544/126; 544/361; 546/94
[58] Field of Search ............ 546/94; 540/597; 514/294, 212, 235.5, 228.2, 252; 544/126, 60, 361

[56] References Cited

U.S. PATENT DOCUMENTS 4,218,453 8/1980 Hannart ............... 546/84

FOREIGN PATENT DOCUMENTS 0167901 1/1986 European Pat. Off. ............ 546/94
0213696 3/1987 European Pat. Off. ............ 546/94
3104884 2/1980 Fed. Rep. of Germany ........ 546/94
7737403 12/1977 France ................. 546/94

OTHER PUBLICATIONS

J. Am. Chem. Soc., vol. 103, pp. 6690-6992 (1981).

Primary Examiner—Mary C. Lee
Assistant Examiner—J. Richter
Attorney, Agent, or Firm—Jacobs & Jacobs

[57] ABSTRACT

A pharmaceutical composition comprising a compound of formula (I) or a pharmaceutically acceptable salt thereof:

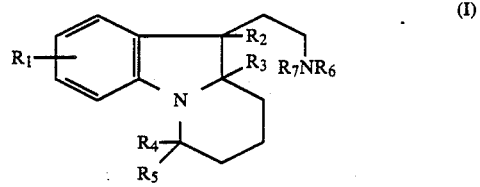

wherein:
$R_1$ is hydrogen, $C_{1-6}$ alkyl, $C_{1-6}$ alkoxy or halogen;
$R_2$ and $R_3$ are both hydrogen or together represent a bond;
$R_4$ is hydrogen and $R_5$ is hydrogen or $R_4$ and $R_5$ together represent an oxo group;
$R_6$ is phenyl $C_{1-7}$ alkanoyl in which the phenyl moiety is optionally substituted by one or two of halogen, nitro, meta- or para-methoxy, methyl or $NR_8R_9$ wherein $R_8$ and $R_9$ are independently hydrogen or $C_{1-6}$ alkyl or $R_8$ and $R_9$ together are $C_{2-6}$ polymethylene, or 3,4-disubstituted by methylenedioxy or ethylenedioxy; or $C_{1-7}$ alkanoyl substituted by $NR_{10}R_{11}$ where $R_{10}$ and $R_{11}$ are independently hydrogen or $C_{1-4}$ alkyl or together are $C_{3-7}$ polymethylene optionally containing a further heteroatom which is oxygen, sulphur or nitrogen substituted by $R_{12}$ where $R_{12}$ is hydrogen, $C_{1-4}$ alkyl or benzyl, and optionally substituted by one or two $C_{1-4}$ alkyl, $C_{2-5}$ alkanoyl, $C_{1-4}$ alkoxycarbonyl, aminocarbonyl optionally substituted by one or two $C_{1-6}$ alkyl groups or by a benzyl group, cyano, phenyl or benzyl and wherein any phenyl or benzyl group is optionally substituted in the phenyl ring by one or two halo, $CF_3$, $C_{1-4}$ alkyl, $C_{1-4}$ alkoxy, cyano or nitro groups; and
$R_7$ is hydrogen or $C_{1-4}$ alkyl;

and a pharmaceutically acceptable carrier.

21 Claims, No Drawings

PYRIDO[1,2-A]INDOLES AND THEIR USE AS CNS AGENTS

This invention relates to compounds having pharmacological activity, to a process for their preparation and their use as pharmaceuticals.

EP-0167901 and EP-0213696 disclose certain secocanthine derivatives having anti-hypoxic activity and/or activity against cerebral oxygen deficiency.

A further group of secocanthine derivatives have been discovered to have anti-ischaemic activity, in particular anti-hypoxic activity and/or activity against cerebral oxygen deficiency and to improve data acquisition or retrieval following transient forebrain ischaemia.

Accordingly, the present invention provides a pharmaceutical composition comprising a compound of formula (I) or a pharmaceutically acceptable salt thereof:

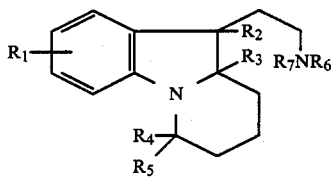

wherein:

$R_1$ is hydrogen, $C_{1-6}$ alkyl, $C_{1-6}$ alkoxy or halogen;

$R_2$ and $R_3$ are both hydrogen or together represent a bond;

$R_4$ is hydrogen and $R_5$ is hydrogen or $R_4$ and $R_5$ together represent an oxo group;

$R_6$ is phenyl $C_{1-7}$ alkanoyl in which the phenyl moiety is optionally substituted by one or two of halogen, nitro, meta- or para-methoxy, methyl or $NR_8R_9$ wherein and $R_9$ are independently hydrogen or $C_{1-6}$ alkyl or $R_8$ and $R_9$ together are $C_{2-6}$ polymethylene, or 3,4-disubstituted by methylenedioxy or ethylenedioxy; or $C_{1-7}$ alkanoyl substituted by $NR_{10}R_{11}$ where $R_{10}$ and $R_{11}$ are independently hydrogen or $C_{1-4}$ alkyl or together are $C_{3-7}$ polymethylene optionally containing a further heteroatom which is oxygen, sulphur or nitrogen substituted by $R_{12}$ where $R_{12}$ is hydrogen, $C_{1-4}$ alkyl or benzyl, and optionally substituted by one or two $C_{1-4}$ alkyl, $C_{2-5}$ alkanoyl, $C_{1-4}$ alkoxycarbonyl, aminocarbonyl optionally substituted by one or two $C_{1-6}$ alkyl groups or by a benzyl group, cyano, phenyl or benzyl and wherein any phenyl or benzyl group is optionally substituted in the phenyl ring by one or two halo, $CF_3$, $C_{1-4}$ alkyl, $C_{1-4}$ alkoxy, cyano or nitro groups; and $R_7$ is hydrogen or $C_{1-4}$ alkyl;

and a pharmaceutically acceptable carrier.

The compounds of formula (I) have anti-ischaemic activity, in particular anti-hypoxic activity and/or activity against cerebral oxygen deficiency. The compounds of formula (I) also improve data acquisition or retrieval following transient forebrain ischaemia. The compounds are therefore useful in the treatment of cerebral vascular and neuronal degenerative disorders associated with learning, memory and cognitive dysfunctions including cerebral senility, multi-infarct dementia and senile dementia of the Alzheimer type.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The invention also provides a method of treatment of cerebrovascular disorders and/or disorders associated with cerebral senility in mammals including humans, which comprises administering to the sufferer an effective amount of a compound of formula (I) or a pharmaceutically acceptable salt thereof.

The invention further provides a method of treatment in mammals including humans of cerebral vascular and neuronal degenerative disorders associated with learning, memory and cognitive dysfunctions including cerebral senility, multi-infarct dementia and senile dementia of the Alzheimer type, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 100 mg. for example 0.2 to 50 mg; and such unit doses may be administered more than once a day, for example two or three times a day, so that the total daily dosage is in the range of about 0.1 to 100 mg/kg; and such therapy may extend for a number of weeks or months.

In a further aspect the invention provides a compound of formula (I), including pharmaceutical salts thereof, for use as an active therapeutic substance.

The invention further provides a compound of formula (I) or a pharmaceutically acceptable salt thereof, for use in the treatment of cerebrovascular disorders and/or disorders associated with cerebral senility.

In another aspect the invention provides a compound of formula (I), including pharmaceutically acceptable salts thereof, for use in the treatment of cerebral vascular and neuronal degenerative disorders associated with learning, memory and cognitive dysfunctions including cerebral senility, multi-infarct dementia and senile dementia of the Alzheimer type.

At the above described dosage range, no toxicological effects are indicated for the compounds of the invention.

Suitable examples of $R_1$ include hydrogen, methyl, ethyl, n- and iso-propyl, n-, sec-, iso- and tert-butyl, methoxy, ethoxy, fluoro and chloro. $R_1$ is preferably hydrogen or methyl, most preferably hydrogen.

$R_2$ and $R_3$ preferably together represent a bond.

Suitable examples of $R_6$ include benzoyl, phenacetyl, 3-phenylpropionyl or 1-methyl-2-phenylacetyl in which the phenyl moiety is optionally substituted by one or two of fluoro, chloro, bromo, amino, methylamino, ethylamino, neo-pentylamino, dimethylamino, diethylamino, di-isopropylamino, 1-piperidyl, 1-pyrrolidyl, ortho- or meta-nitro, meta or para-methoxy, or methyl, or 3,4-disubstituted by methylenedioxy.

Suitable examples of cyclic aminoalkanoyl $R_6$ include $NR_{10}R_{11}C_{1-7}$ alkanoyl where $R_{10}$ and $R_{11}$ together form a piperidine, pyrrolidine, piperazine or morpholine ring. Suitable examples of optional substituents on cyclic amino $C_{1-7}$ alkanoyl $R_6$ include one or two $C_{1-4}$ alkyl groups such as methyl, ethyl, n- and iso-propyl, and n-, sec-, iso- and t-butyl. Suitable examples of cyclic $NR_{10}R_{11}$ includes 1-piperidyl, 2-methyl-1-piperidyl, 3-methyl-1-piperidyl, 3,5-dimethyl-1-piperidyl, 2,6-dimethyl-1-piperidyl, 2,5-dimethyl-1-pyrrolidyl, 2,4-dimethyl-1-pyrrolidyl and 1-morpholinyl.

Suitable examples of acyclic amino alkanoyl $R_6$ include $C_{1-4}$ alkyl amino $C_{1-7}$ alkanoyl and di-$C_{1-4}$ alkylamino $C_{1-7}$ alkanoyl, such as methylamino-, ethylamino-, n- or iso-propylamino-, iso-butylamino-, dimethylamino-, diethylamino, di-n- or iso-propylamino- and di-iso-butylamino $C_{1-7}$ alkanoyl.

Preferably $R_6$ is benzoyl or 1-methyl-2-phenylacetyl optionally monosubstituted in the phenyl moiety by $NR_8R_9$; or $C_{3-7}$ alkanoyl, such as $C_{4-6}$ or $C_{5-7}$ alkyl, substituted by $NR_{10}R_{11}$, suitable carbon chain lengths in $R_6$ including $C_3$, $C_4$ and $C_5$. When $NR_{10}R_{11}$ is a cyclic moiety, it preferably comprises 5 to 7 ring atoms, more preferably 5 or 6 ring atoms.

Suitable examples of $R_7$ include hydrogen, methyl, ethyl, n- and iso-propyl, n-, sec-, iso- and tert-butyl, preferably hydrogen.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

There is a favourable group of compounds within formula (I) of formula (II):

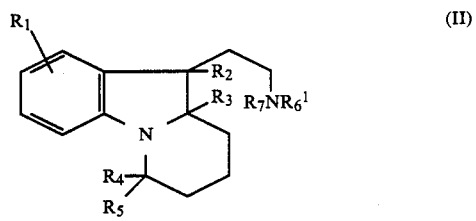

wherein $R_1$, $R_2$, $R_3$, $R_4$, $R_5$ and $R_7$ are as defined in formula (I) and $R_6^1$ is phenyl $C_{1-7}$ alkanoyl optionally monosubstituted by fluoro, chloro, bromo, $NR_8R_9$ where $R_8$ and $R_9$ are as defined in formula (I), methoxy or nitro; or $NR_{10}^1 R_{11}^1 C_{1-7}$ alkanoyl where $R_{10}^1$ and $R_{11}^1$ together are $C_{3-7}$ polymethylene optionally containing a further heteroatom as defined above for $R_{10}$ and $R_{11}$ and optionally substituted by one or two $C_{1-4}$ alkyl groups.

Suitable and preferred values for $R_1$, $R_2$, $R_3$, $R_6^1$, $R_7$, $R_8$ and $R_9$ are as described under formula (I) for $R_1$, $R_2$, $R_3$, $R_6$, $R_7$, $R_8$ and $R_9$.

There is a sub-group of compounds within formula (II) of formula (IIa):

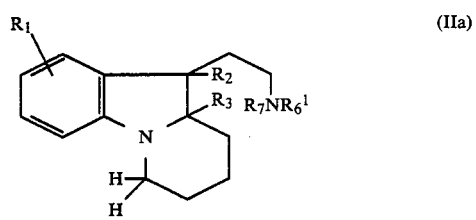

wherein $R_1$, $R_2$, $R_3$, $R_6^1$ and $R_7$ are as defined in formula (II).

Suitable and preferred values for the variables are as described for the corresponding variables under formula (I).

There is a sub-group of compounds within formula (IIa) of formula (IIb):

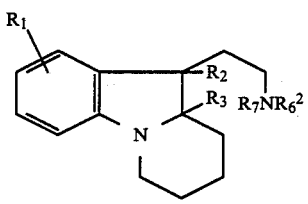

(IIb)

wherein $R_1$, $R_2$, $R_3$ and $R_7$ are as defined in formula (I) and $R_6^2$ is phenyl $C_{1-4}$ alkanoyl optionally mono-substituted by $NR_8R_9$ where $R_8$ and $R_9$ are as defined in formula (I); or (1-piperidyl)$C_{1-7}$ alkanoyl substituted by one or two $C_{1-4}$ alkyl groups.

Suitable and preferred values for the variables are as described for the corresponding variables under formula (I).

Preferably $R_6^2$ is benzoyl or 1-methyl-2-phenylacetyl optionally meta- or para-substituted by amino optionally substituted by one or two methyl or ethyl groups; or 5-(3,5-dimethyl-1-piperidyl)-1-oxo-pentyl.

There is another sub-group of compounds within formula (IIa) of formula (IIc):

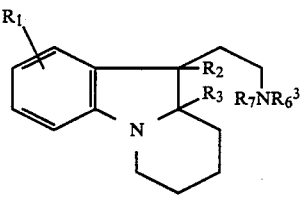

(IIc)

wherein $R_1$, $R_2$, $R_3$, and $R_7$ are as defined in formula (I) and $R_6^3$ is -CO(CH$_2$)$_4$NR$_{10}^1$R$_{11}^1$ where $R_{10}^1$ and $R_{11}^1$ are as defined in formula (II).

Preferably $R_1$ is hydrogen.

Preferably $R_2$ and $R_3$ represent a bond.

Preferably $R_7$ is hydrogen.

There is a further group of compounds within formula (II) of formula (IId):

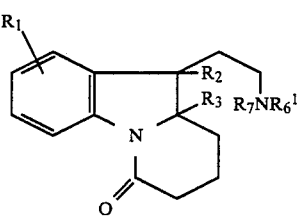

(IId)

wherein $R_6^1$ is as defined in formula (II) and the remaining variables are as defined in formula (I).

Suitable and preferred values for $R_6^1$ and $R_7$ are as described under formulae (II) and (IIa).

Another subgroup of compounds within formula (I) is of formula (III):

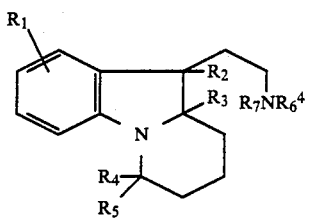

(III)

wherein $R_1$, $R_2$, $R_3$, $R_4$, $R_5$ and $R_7$ are as defined in formula (I) and $R_6^4$ is $NR_{10}^2 R_{11}^2$ $C_{1-7}$ alkanoyl where $R_{10}^2$ and $R_{11}^2$ are independently hydrogen or $C_{1-4}$ alkyl.

Preferably $R_6^4$ is —CO(CH$_2$)$_4$NR$_{10}^2$R$_{11}^2$ where $R_{10}^2$ and $R_{11}^2$ are as defined.

The invention further provides novel compounds within formula (I).

Where compounds of formula (I) can exist in more than one stereoisomeric form, the invention extends to each of these forms and to mixtures thereof.

Compounds of formula (I) described in EP-0167901 and EP-0213696 useful in the invention include:
6-Oxo-10-[2-(3-nitrobenzoyl)aminoethyl]-6,7,8,9-tetrahydropyrido[1,2-a]indole
6-Oxo-10-[2-(3-aminobenzoyl)aminoethyl]-6,7,8,9-tetrahydropyrido[1,2-a]indole
6-Oxo-10-[2-(5-[3,5-dimethyl-piperidyl-(1)]valeryl)aminoethyl]-6,7,8,9-tetrahydropyrido[1,2-a]indole
10-[2-(5-[3,5-Dimethyl piperidyl-(1)]valeryl) aminoethyl]-6,7,8,9-tetrahydropyrido[1,2-a]indole
10-[2-(5-Dimethylaminovaleryl)aminoethyl]-6,7,8,9-tetrahydropyrido[1,2-a]indole
10-[2-(5-[Piperidyl-(1)]valeryl)aminoethyl]-6,7,8,9-tetrahydropyrido[1,2-a]indole
10-[2-(5-[Pyrrolidinyl-(1)]valeryl)aminoethyl]-6,7,8,9-tetrahydropyrido[1,2-a]indole
10-[2-(5-[Morpholinyl-(1)]valeryl)aminoethyl]-6,7,8,9-tetrahydropyrido[1,2-a]indole
6-Oxo-10-[2-(3-piperidinobenzoyl)aminoethyl]-6,7,8,9-tetrahydropyrido[1,2-a]indole
6-Oxo-10-[2-(3-diisopropylaminobenzoyl)aminoethyl]-6,7,8,9-tetrahydropyrido[1,2-a]indole
6-Oxo-10-[2-(3-pyrrolidinobenzoyl)aminoethyl]-6,7,8,9-tetrahydropyrido[1,2-a]indole
6-Oxo-[2-benzoylaminoethyl]-6,7,8,9,-tetrahydropyrido[1,2-a]indole
6-Oxo-10-[2-(3-dimethylaminobenzoyl)aminoethyl]-6,7,8,9-tetrahydropyrido[1,2-a]indole
2-Methyl-6-oxo-10-[2-benzoylaminoethyl]-6,7,8,9-tetrahydropyrido [1,2-a]indole.

Compounds D1 and D2 described hereinafter are also useful in the present invention.

A process for the preparation of a compound of formula (I), or a pharmaceutically acceptable salt thereof comprises the conversion of a compound of formula (V):

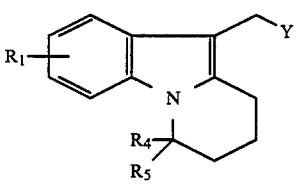

(V)

wherein $R_1$, $R_4$ and $R_5$ are as defined in formula (I) and Y is a group convertible to CH$_2$NR$_6'$R$_7'$ where $R_6'$ is $R_6$ as defined in formula (I) or a group convertible thereto, and $R_7'$ is an amino protecting group or $R_7$ as defined in formula (I), into a compound formula (Va):

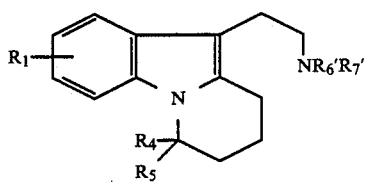

and thereafter, optionally and as necessary, converting $R_6'$ when other than $R_6$ into $R_6$, removing any $R_7'$ amino protecting group, interconverting $R_6$ and/or $R_7$ to other $R_6$ or $R_7$, reducing the $R_2/R_3$ bond and/or, when $R_4/R_5$ is oxo, reducing the oxo group to give a compound wherein $R_4$ and $R_5$ are both hydrogen and/or forming a pharmaceutically acceptable salt.

Y may be conventional amine precursor. Suitable examples include CN, COQ where Q is H or a leaving group such as halo, $C_{1-4}$ alkoxy or carboxylic acyloxy, and $CH_2L$ where L is $CON_3$, $N_3$, $NO_2$ or X where X is a leaving group such as hydroxy, halo, $C_{1-4}$ alkoxy, $C_{1-4}$ alkanoyloxy, $C_{1-4}$ alkoxycarbonyloxy, tosyloxy or mesyloxy.

The reaction converting the compound of formula (V) into that of formula (Va) may be carried out under the conventional conditions appropriate to the particular group Y in formula (V).

Thus, when Y is $CH_2CON_3$, the conversion is a Curtius degradation carried out conventionally, by heating in dry inert solvent, such as benzene, and then subsequent hydrolysis of the thus formed isocyanate under acid conditions.

When Y is CN, the conversion is a reduction to the primary amine, for example with a reducing agent such as diborane or $LiAlH_4$ at elevated temperature and in an inert solvent such as tetrahydrofuran, or with hydrogen over Raney nickel in the presence of ammonia at ambient temperature in a polar solvent such as methanol.

When Y is CHO, the conversion is a condensation with hydroxylamine followed by reduction of the thus formed oxime over a metallic catalyst, or is a reductive amination with a primary or secondary amine using a reducing agent such as $NaBH_3CN$ in a polar solvent such as $CH_2Cl_2/CH_3OH$ at elevated temperature.

Alternatively the intermediate imine may be prepared in a non polar solvent such as benzene in the presence of an acid catalyst e.g. p-toluenesulphonic acid and reduced with a reducing agent such as $NaBH_4$.

When Y is COQ where Q is a leaving group, the conversion is a nucleophilic substitution by ammonia or a primary or secondary amine under conventional conditions appropriate for leaving group Q, followed by reduction of the resulting amide with e.g. $LiAlH_4$ in an inert solvent such as tetrahydrofuran at elevated temperature followed by work up. For example, when Q is halo such as chloro, the nucleophilic substitution may be carried out at ambient or lower temperature in the presence of an acid acceptor such as triethylamine in a polar solvent such as $CH_2Cl_2$, followed by work up to give the amide which may be reduced as just described.

When Y is $CH_2N_3$, the conversion is a reduction of the azide to the primary amine with e.g. hydrogen over a metallic catalyst.

When Y is $CH_2NO_2$, the conversion is a reduction of the nitro group to the primary amine with a reducing agent such as $LiAlH_4$, or hydrogen over Raney nickel or Pd/C catalyst in a polar solvent such as ethanol.

When Y is $CH_2X$, the conversion is a nucleophilic substitution by ammonia or a primary or secondary amine or azide ion, under conventional conditions appropriate for the leaving group X. Thus, when X is hydroxy, it is first converted into a good leaving group such as mesylate or tosylate (using mesyl or tosyl chloride respectively) or chloride (using $SOCl_3$). The nucleophilic substitution may be carried out at elevated temperature in a polar solvent such as acetonitrile in the presence of an acid acceptor such as diisopropyl ethylamine. Alternatively, the leaving group may be substituted by nitrile to yield a compound of formula (V) where $Y=CH_2CN$. Hydrolysis and conversion by conventional methods yields a compound where $Y=CH_2CON_3$ via the acid as described hereinafter.

Suitable examples of $R_6'$ include hydrogen, an amino protecting group and $R_6$ with any amino substituent on a phenyl moiety protected.

In the resulting compound of formula (Va) in the case where $R_6'$ or $R_7'$ is an amino protecting group such as $C_{1-6}$ alkoxy carbonyl, aryloxycarbonyl, $C_{1-6}$ alkanoyl or phenyl $C_{1-7}$ alkanoyl, the protecting group may be removed by conventional procedures. Alternatively, $R_7'$ alkanoyl may be converted directly to alkyl or phenyl alkyl $R_7$ (as appropriate) by reduction, e.g. with $LiAlH_4$ and $AlCl_3$.

When $R_6'$ is an $R_6$ group with a protected amino moiety, again the protecting group may be removed conventionally or the protected $R_6$ be converted to the desired $R_6$ group by reduction as in the preceding paragraph The conversion of any $R_6'$ amino protecting group to $R_6$ via the $R_6'$ hydrogen intermediate or the conversion of $R_6'$ hydrogen to $R_6$, may be carried out by conventional amine acylation. The interconversion of an $R_7$ hydrogen atom may be carried out by conventional amine alkylation or, more preferably, by acylation followed by reduction of the amide, or by reductive alkylation.

Acylation may be carried out using the appropriate acyl chloride or anhydride and, if necessary, the subsequent reduction of the resulting amide with $LiAlH_4$ in the presence of $AlCl_3$.

The reductive alkylation procedure is preferably carried out by heating with the aldehyde or ketone in an organic acid, such as acetic acid, then reducing the product in situ using an alkaline borohydride such as sodium borohydride or cyanoborohydride. The reaction can also be carried out in an alcohol, in which case the reduction can be carried out either chemically, for example with a borane such as trimethylammoniumborane or an alkaline borohydride or with hydrogen in the presence of a catalyst such as Raney nickel.

It is also possible to use an aprotic solvent, for example an aromatic solvent such as benzene or toluene, the water formed being eliminated either at room temperature by means of a drying-agent or under reflux heating of the solvent by means of a Dean-Stark water-separator; the reduction can then be expediently carried out with hydrogen in the presence of a catalyst such as palladiated carbon or platinum oxide. These methods may be subject to certain limitations, depending on the nature of the aldehyde or ketone used.

It is also possible to use a more universal method. For example, the $R_7$ hydrogen compound and the aldehyde or ketone to be condensed are dissolved in a mixture of solvents which can advantageously be a methanol-dichloromethane mixture in the presence of a complex reducing agent such as quaternary ammonium cyanoborohydride or, more simply, an alkaline cyanoborohydride solubilised by a phase-transfer agent, for example sodium cyanoborohydride and aliquat 336(Cf. Hutchins, R. O. and Markowitz, M., Journal of Organic Chemistry 1981, 46, pp.3571-3574).

The acylation may introduce the required moiety $NR_{10}R_{11}$ in the alkanoyl substituent $R_6$ directly, or alternatively by way of an amine precursor $Y^1$ which is convertible to $CH_2NR_{10}'R_{11}'$ (where $R_{10}'$ and $R_{11}'$ are $R_{10}$ and $R_{11}$ or groups convertible thereto) analogously to the conversion of the group Y in the compound of formula (V). For example, the amine precursor $Y^1$ may be of the formula $CH_2X^1$ where $X^1$ is a leaving group as defined for X above, such as halo e.g chloro which can be subsequently displaced by a compound $HNR_{10}R_{11}$.

It will be appreciated that compounds of formula (I) wherein $R_6$ is substituted phenyl $C_{1-7}$ alkanoyl may be interconverted by conventional procedures including aromatic substituents. For example a compound of formula (I) wherein $R_6$ is benzoyl substituted by amino may be prepared from a compound wherein $R_6$ is benzoyl substituted by nitro, by catalytic reduction, for example in the presence of Raney nickel, or Pd/C and trifluoroacetic acid.

A compound of formula (I) wherein $R_6$ is benzoyl substituted by substituted amino may be prepared from the corresponding amine by conventional procedures. Thus when $R_8$ or $R_9$ is an alkyl group, conventional amine alkylation may be employed.

The reduction of the $R_2/R_3$ bond may be carried out conventionally by the use of an alkaline borohydride in a polar aprotic solvent such as dimethylsulphoxide or by nitromethane in the presence of a strong organic acid such as methanesulphonic acid or in pure trifluoroacetic acid. Alternatively the bond may be reduced catalytically with hydrogen over platinum oxide catalyst in a solvent permitting protonation of the indolic nitrogen, such as ethanol containing fluoroboric acid or acetic acid containing trifluoroacetic acid.

When $R_4$ and $R_5$ together form an oxo group, compounds wherein $R_4$ and $R_5$ are both hydrogen may be prepared by reduction of the $R_4/R_5$ oxo group in formula (I) using a mixed hydride complexed with a Lewis acid, for example, the complex aluminium lithium aluminium chloride hydride in an inert solvent such as diethyl ether. When an $R_7$ group other than hydrogen is introduced initially by acylation to give the amide, simultaneous reduction of the $R_4/R_5$ oxo group and the amide moiety may be effected by appropriate choice of reducing agent, for example the mixed hydride complexed with a Lewis acid just described.

When $R_2$ and $R_3$ together form a bond and $R_4$ and $R_5$ together form an oxo group, simultaneous reduction of the double bond and the oxo group may be effected by the use of an alkaline borohydride as described above for the reduction of an $R_2/R_3$ bond.

It will be appreciated that these conversions may take place in any desired or necessary order. It will also be appreciated that conversions involving reduction should, preferably be carried out prior to the introduction of $R_6$ so as to avoid reduction of the amide.

Pharmaceutically acceptable salts of the compounds of formula (I) may be formed conventionally by reaction with the appropriate acid such as described above under formula (I).

The invention also provides a process for the preparation of novel compounds of formula (I), or a pharmaceutically acceptable salt thereof which process comprises the conversion of the compound of formula (V) as hereinbefore defined to the compound of formula (Va) as hereinbefore defined and thereafter, optionally and as necessary, converting $R_6'$ when other than $R_6$ into $R_6$, removing any $R_7'$ amino protecting group, interconverting $R_6$ and/or $R_7$ to other $R_6$ or $R_7$, reducing the $R_2/R_3$ bond and/or, when $R_4/R_5$ is oxo, reducing the oxo group to give a compound wherein $R_4$ and $R_5$ are both hydrogen and/or forming a pharmaceutically acceptable salt.

Compounds of formula (V) in which Y is $CH_2CON_3$ may be prepared by the formation of the acid chloride followed by reaction of azide ion on an acid of formula (VI):

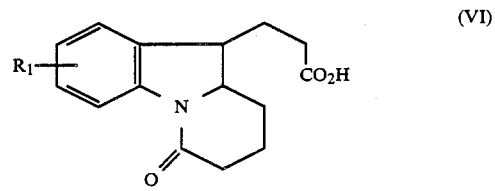

(VI)

This method is described in J. Am. Chem. Soc. 1981, 103, 6990-6992.

Acids of formula (VI) are known or may be prepared by conventional methods. For example, a phenylhydrazine is condensed with 4-oxoazelaic acid (ref. Von Pechmann et. al. Berichte 1904, 37, p 3816). The hydrazone thus obtained is subjected to a Fischer cyclisation to give the acid of formula (VI).

Compounds of formula (V) in which $R_4$ and $R_5$ are both hydrogen may be prepared by the reaction of a compound of formula (VII):

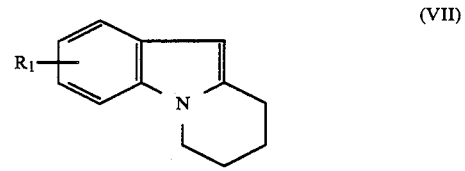

(VII)

with
(i) $ClCOCOR_{13}$, where $R_{13}$ is alkoxy such as ethoxy or halo such as chloro, followed by reduction with $LiAlH_4$ to give a compound of formula (V) where Y is $-CH_2OH$ which may subsequently be reacted with azide ion to give the corresponding compound where Y is $-CH_2N_3$;
(ii) $CH_2=CH-R_{14}$, where $R_{14}$ is a 1-carbonyl containing group or cyano, under basic conditions, followed by hydrolysis and reaction on the resulting acid group by azide ion as described above, to give a compound of formula (V) where Y is $-CH_2CON_3$;
(iii) formaldehyde in the presence of dimethylamine followed by reaction of cyanide ion on the resulting tertiary amine, if necessary after quaternization, to give a compound of formula (V) where Y is $-CN$;

(iv) CH$_2$=CHNO$_2$ under basic conditions to give a compound of formula (V) where Y is CH$_2$NO$_2$.

Compounds of formula (VII) can be prepared according to Hans Zimmer, J. Heterocylic Chemistry 21, 623(1984).

Compounds of formula (V) in which Y is CHO may be prepared from the corresponding compound in which Y is CN by a variety conventional procedures such as, for example, reaction with diisobutylaluminium hydride.

Compounds of formula (V) in which Y is COQ where Q is a leaving group may be prepared from the corresponding compound in which Y is CN by, for example, hydrolysis under acid conditions of the nitrile to give the corresponding acid, followed by conversion of the hydroxyl group to a leaving group Q such as chloro with a chlorinating agent such as oxalyl chloride. Interconversion of leaving groups Q may be carried out conventionally.

Compounds of formula (V) in which R$_4$ and R$_5$ are both hydrogen and Y is —CH$_2$CN, may alternatively be prepared by homologation and reduction of a compound of formula (VIII):

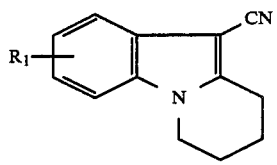

(VIII)

prepared according to D. N. Reinhoudt et al., Tetrahedron Letters 26 (5) 1985, 685–8. The nitrile is first reduced to the amine which is quaternised and reacted with cyanide ion to give the relevant compound of formula (V).

In the formulae (VI),(VII) and (VIII) above, R$_1$ is as defined in formula (I).

The following examples and pharmacological data illustrate the invention and the following descriptions illustrate the preparation of intermediates thereto.

DESCRIPTION 1

10-[2-(4-Nitrobenzoyl)aminoethyl]-6,7,8,9-tetrahydropyrido[1,2-a]indole (D1)

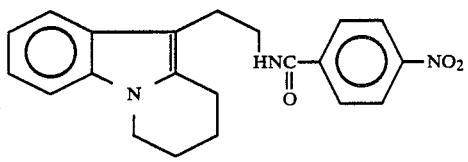

A solution of 10 g p-nitrobenzoyl chloride in 50 ml of chloroform was added dropwise to a suspension of 10-(2-aminoethyl)-6,7,8,9-tetrahydropyrido[1,2-a]indole hydrochloride (E19 of EP-0167901) and 25 ml triethylamine in 300 ml chloroform. The mixture was left to stand for 2 hours at room temperature, then shaken with citric acid solution, sodium carbonate solution and brine, dried and evaporated. Crystallisation from diisopropyl ether yielded 13.2 g
m.p: 184°–5° C.

DESCRIPTION 2

10-[2-(4-Aminobenzoyl)aminoethyl]-6,7,8,9-tetrahydropyrido[1,2-a]indole hydrochloride (D2)

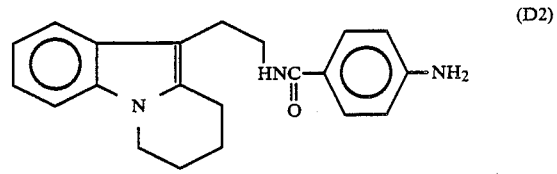

Compound D1 was hydrogenated at room temperature at a pressure of 4 bar for 24 hours in trifluoroacetic acid in the presence of 1 g Pd/C.

The catalyst was filtered off, the solution concentrated, taken up in methylene chloride, shaken with sodium carbonate solution, dried, evaporated and the amine acidified with ethanol/HCl giving 9.6 g product.
m.p: 210° C. dec.

Nmr (DMSO D6) δ=1.7–2.3 [4]m; 4 [2]tr, J=6 Hz; 6.9–8 [8]m.

DESCRIPTION 3

10-[2-(4-Chloro-1-oxobutyl)aminoethyl]-6-oxo-6,7,8,9-tetrahydropyrido[1,2-a]indole (D3)

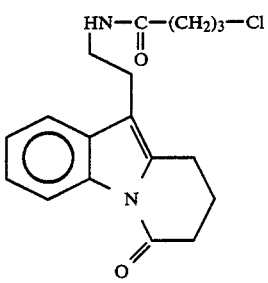

D3 was prepared analogously to D3 in EP-0213696 from 6-oxo-10-(2-aminoethyl)-6,7,8,9tetrahydropyrido[1,2-a]indole (compound D4 of EP-0167901) and 4-chlorobutyric acid chloride.
m.p. 127° C.

NMR CDCl$_3$ δ=8.45 [1]m; 7.35 [3]m; 5.88 [1]m; 3.55 [4]m; 2.78 [6]m; 2.15 [6]m.

DESCRIPTION 4

10-[2-(6-Bromo-1-oxohexyl)aminoethyl]-6-oxo-6,7,8,9-tetrahydrophyrido[1,2-a]indole(D4)

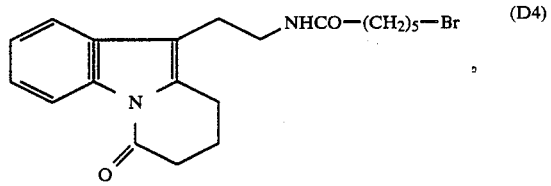

Compound D4 was prepared analogously to D3 from 6-oxo-10-(2-aminoethyl)-6,7,8,9-tetrahydropyrido [1,2-a]indole (compound D4 of EP-0167901) and 6-bromohexanoic acid chloride.
Yield: 34%
m.p: 110°–111° C.

DESCRIPTION 5

10-[2-(6-Bromo-1-oxohexyl)aminoethyl]-6,7,8,9-tetrahydropyrido[1,2-a]indole(D5)

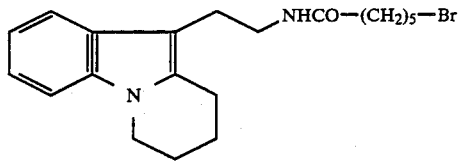

To the cooled mixture of 42.8 g (0.2 mole) 10-(2-aminoethyl)-6,7,8,9-tetrahydropyrido[1,2-a]indole (E19 of EP-0167901) and 20.2 g (0.2 mole) triethylamine, a solution of 42.7 g (0.2 mole) 6-bromohexanoic acid chloride in 400 ml chloroform was added dropwise. The temperature was adjusted to be between −10° C. and +5° C. After the addition was complete, the reaction mixture was stirred at the above temperature for ½ hour, and then poured into crushed ice. The layers were separated and the organic phase washed with water and dried. The solvent was evaporated and the residue crystallised from ethyl acetate.

Yield: 46.2 g, 59%
m.p: 118°–119° C.

DESCRIPTION 6 to 8

The compounds were prepared by an analogous procedure to that of Description 5:

10-[2-(4-Chloro-1-oxobutyl)aminoethyl]6,7,8,9-tetrahydropyrido[1,2-a]indole(D6)

Yield: 80%
m.p: 120° C.

10-[2-(3-Chloro-1-oxopropyl)aminoethyl]-6,7,8,9-tetrahydropyrido[1,2-a]indole (D7)

Yield: 75%.

10-[2-(2-Chloro-1-oxoethyl)aminoethyl]-6,7,8,9-tetrahydropyrido[1,2-a]indole(D8)

DESCRIPTION 9

10-(2-N-Methylaminoethyl)-6,7,8,9-tetrahydropyrido[1,2-a]indole(D9)

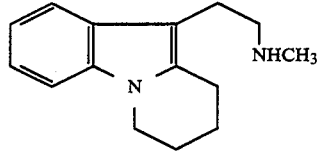

A mixture of 8.6 g (0.038 mole)6-oxo-10-(2-aminoethyl)-6,7,8,9-tetrahydropyrido[1,2-a]indole (compound D4 of EP-0167901) and 9.0 g (0.12 mole) ethyl formate was refluxed over 2 hours. The excess of ethyl formate was evaporated. The residue was dissolved in ethyl acetate, shaken with sodium carbonate solution, dried and evaporated yielding 9.5g (97% of theory) 6-oxo-10-(2-N-formylaminoethyl)-6,7,8,9-tetrahydropyrido[1,2-a]indole, which was dissolved in 100 ml THF and added dropwise to a cooled suspension of 4.9 g LiAlH$_4$ and 6.4 g AlCl$_3$ in 100 ml diethylether at −10° C. The reaction mixture was stirred 2 hours at room temperature until the reduction was complete. The excess LiAlH$_4$/AlCl$_3$ was hydrolyzed with NaOH solution at −5° C. The precipitate was filtered off and washed with ether. The filtrate was shaken with water and dilute HCl. The acidic extract was made alkaline with sodium carbonate solution and extracted with ether. The ether extract was dried and evaporated yielding 6.0 g (71% of theory) yellow oily D9 base.

calc.: C 78.95 H 8.77 N 12.28
found: C 78.97 H 9.06 N 12.04

The compound was converted to the hydrochloride.
m.p: 252°–254° C. (decomp)

DESCRIPTION 10

10-[2-(4-Chloro-1-oxobutyl-N-methylaminoethyl]-6,7,8,9-tetrahydrophyrido[1,2-a]indole (D10)

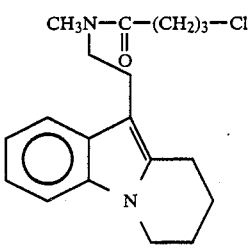

To a cooled mixture of 5.0 g (0.022 mole) D9 in 30 ml chloroform was dropped 2.12 g (0.022 mole) triethylamine and a solution of 3.7 g 4-chlorobutyric acid chloride in 10 ml chloroform. After the addition was complete the reaction mixture was stirred 30 min. at room temperature and then poured onto crushed ice. The layers were separated and the organic phase was dried, filtered and evaporated, yielding 7 g (96% of theory) oily D10.

The compound crystallized by standing at room temperature.

m.p: 76° C.

EXAMPLE 1

10-[2-(3-Nitrobenzoyl)aminoethyl]-6,7,8,9tetrahydropyrido[1,2-a]indole semihydrate (E1)

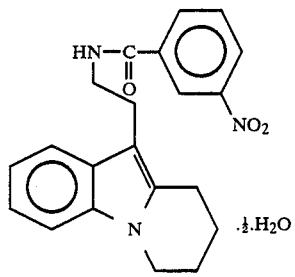

The synthesis is analogous to Description 1
4 g m-nitrobenzoyl chloride.
4 g amine hydrochloride E19 of EP-0167901.
8 ml triethylamine.
140 ml methylene chloride.
Yield: 5.1 g orange crystals containing 0.5 mol water.
m.p: 156° C.
NMR (CDCl$_3$) δ=1.7–2.3 [4]m; 2.7–3.2 [4]m; 3.5–3.9 [2]m; 4.15 [2]tr, J=6 Hz; 6.3 [1]s broad exchange; 7.0–8.5 [8]m.

EXAMPLE 2

10-[2-(3-Aminobenzoyl)aminoethyl]-6,7,8,9-tetrahydropyrido[1,2-a]indole hydrochloride (E2)

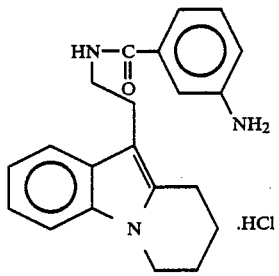

2.7 g E1 was shaken in a hydrogenator overnight in 90 ml methanol and 10 ml trifluoroacetic acid and 0.3 g 10% Pd on charcoal. The solution was filtered, made alkaline with sodium carbonate solution, extracted with methylene chloride and evaporated. The product was isolated as the hydrochloride.

Yield: 2.8 g.
m.p: 174° C.

NMR DMSO d6) $\delta=1.5–2.2$ [4]m; 2.7–3.1 [4]m; 3.2–3.7 [2]m; 4.0 [2]tr, J=6 Hz; 6.8–7.7 [8]m; 8.6 [1]tr, J=7 Hz (exchange); 8.9 [3]s broad (exchange).

EXAMPLE 3

10-[2-(5-Dimethylamino-1-oxopentyl)aminoethyl]-6-oxo-6,7,8,9-tetrahydropyrido[1,2-a]indole (E3)

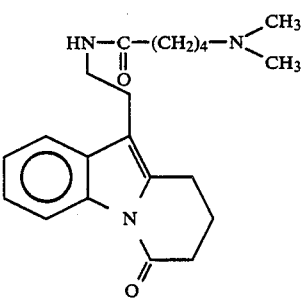

15 g 6-Oxo-10-[2-(5-chlorovaleryl)aminoethyl]-6,7,8,9tetrahydropyrido[1,2-a]indole (D 3 of EP-0213696), 14.6 ml diisopropylethylamine, 1 g KI and 3.5 g dimethylamine hydrochloride were dissolved in 100 ml DMF and stirred for 48 hours at room-temperature. After further stirring for 7 hours at 40° C. the reaction mixture was dissolved with water and extracted with ethyl acetate. After acid-base separation the product was crystallised from diisopropylether.

Yield: 4 g
m.p: 115°–116° C.;
NMR (CDCl3) $\delta=8.45$ [1]m; 7.35 [3]m; 6.10 [1]m, broad; 3.50 [2]q, J=6.4 Hz; 2.82 [6]m; 2.20 [12]m; 1.55 [4]m.

EXAMPLE 4

10-[2-(5-Piperidinyl-(1)-1-oxopentyl)aminoethyl]-6-oxo-6,7,8,9-tetrahydropyrido[1,2-a]indole hemihydrate (E4)

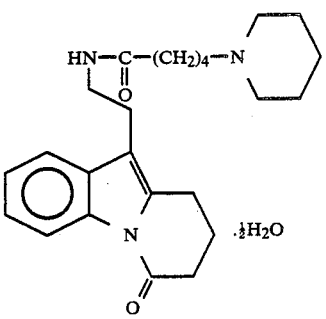

10 g D3 of EP-0213696, 7.8 ml.piperidine, 1.5 g KI and 5.1 ml diisopropylethylamine were dissolved in 100 ml acetonitrile and stirred for 17 hours at room temperature. After further stirring at 60° C. for 12 hours the reaction mixture was diluted with 300 ml water and extracted with CH2Cl2. After acid-base separation the product was crystallised from ethyl acetate.

Yield: 8 g
m.p: 112° C.
NMR (CDCl3) $\delta=8.42$ [1]m; 7.35 [3]m; 6.08 [1]m, broad; 3.50 [2]q, J=6.5 Hz; 2.85 [6]m; 2.25 [10]m; 1.55 [10]m.

calc.: C 71.26 H 8.47 N 10.39
found: C 70.84 H 8.30 N 10.42.

EXAMPLE 5

10-[2-(5-[3-Methylpiperidinyl-(1)]-1-oxopentyl) aminoethyl]-6-oxo-6,7,8,9-tetrahydropyrido[1,2-a]indole (E5)

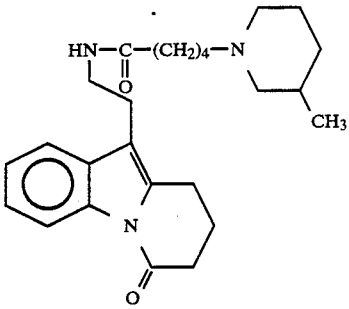

7 g 6-Oxo-10-[2-(5-chlorovaleryl)aminoethyl]-6,7,8,9tetrahydropyrido[1,2-a]indole (D3 of EP-0213696), 4.5 g 3-methylpiperidine, 0.5 g KI and 5.1 ml diisopropylethylamine were dissolved in 100 ml DMF and heated for 12 hours at 55+ C.

After the addition of 300 ml water and extraction with ethylacetate, the organic layer was extracted with citric acid. The acidic phase was made alkaline with sodium carbonate and extracted with CH2Cl2. The crude product was purified by column chromatography (CH2Cl2) and crystallised from ethyl acetate/ether.

Yield: 5.2 g
m.p: 103°–104° C.

NMR (CDCl$_3$) δ=8.47 [1]m; 7.30 [3]m; 6.00 [1]m; 3.48 [2]q, J=6.3 Hz; 2.80 [8]m; 2.15 [7]m; 1.55 [10]m; 0.80 [3]d, J=6 Hz.
calc.: C 73.31 H 8.61 N 10.26
found: C 73.76 H 8.64 N 10.26.

EXAMPLE 6

10-[2-(4-[3,5-Dimethylpiperidinyl-(1)]-1-oxobutyl-)aminoethyl]-6-oxo-6,7,8,9-tetrahydropyrido[1,2-a]indole hydrochloride hydrate (E6)

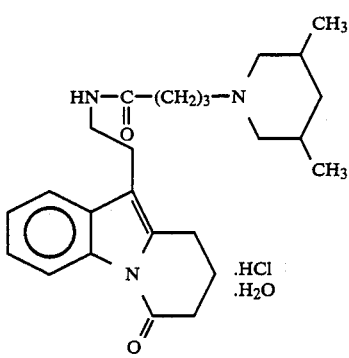

10 g D3, 0.5 g KI and 16 ml 3,5-dimethylpiperidine were dissolved in 100 ml acetonitrile and stirred for 28 hours at room temperature. Then the solvent was evaporated and the product purified by column chromatography (CH$_2$Cl$_2$).

The compound was converted to the hydrochloride and crystallised from ethyl acetate.

Yield: 3.7 g
m.p: 126° C.
NMR (d$_6$-DMSO) δ=10.85 [1]s, broad; 8.25 [2]m; 7.60 [1]m; 7.30 [2]m; 3.55–1.50 [24]m; 0.90 [6]d, J=6 Hz.
calc.: C 64.71 H 8.25 N 9.05 Cl 7.64
found: C 64.67 H 8.10 N 9.25 Cl 7.72.

EXAMPLE 7

10-[2-(4-[3,5-Dimethylpiperidinyl-(1)]-1-oxobutyl)-aminoethyl]-6,7,8,9-tetrahydropyrido[1,2-a]indole hydrochloride (E7)

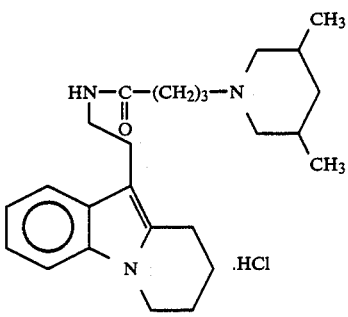

1 g LiAlH$_4$ were suspended in 100 ml ether/THF, cooled to −15° C. and 2.1 g AlCl$_3$ were added in small portions. 6.5 g E6 were dissolved in 50 ml THF and added dropwise to the reaction mixture. After 30 minutes 2.5 M NaOH was added with caution until the solution was alkaline. The precipitate was filtered off and carefully washed with methanol. The filtrate was evaporated and the crude product purified by column chromatography (CH$_2$Cl$_2$/5%CH$_3$OH). The product crystallised as a hydrochloride from ethyl acetate.
m.p: 183° C.

NMR (d$_6$-DMSO) δ=11.05 [1]s, broad; 8.28 [1]tr, broad; 7.55–6.85 [4]m; 4.00 [2]tr, J=4.5 Hz; 3.40–1.50 [24]m; 0.85 [6]d, J=6 Hz.

EXAMPLE 8

10-[2-(2-Phenylacetyl)aminoethyl]-6,7,8,9-tetrahydropyrido[1,2-a]indole (E8)

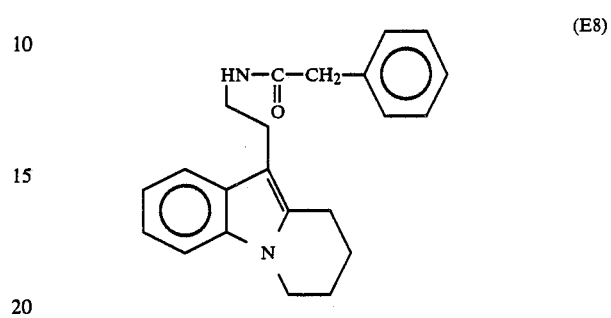

10.5 g E19 of EP-0167901 were dissolved in 200 ml CH$_2$Cl$_2$ and 10 ml triethylamine were added. Then 7.73 g phenylacetic acid chloride were added dropwise to the mixture. After stirring for 2 hr the reaction mixture was washed with dilute HCl-solution, with sodium carbonate and with brine. The organic layer was dried and evaporated. The product crystallised from diisopropylether.

Yield: 8.9 g
m.p: 126° C.
NMR (DMSO-d$_6$) δ=7.24 [9]m; 5.42 [1]s, broad; 4.00 [2]tr, J=6.3 Hz; 4.47 [4]m; 2.75 [4]m; 1.92 [4]m.
calc.: C 79.48 H 7.28 N 8.43
found: C 79.20 H 7.31 N 8.42.

EXAMPLE 9

10-[2-(4-Dimethylaminobenzylcarbonyl)aminoethyl]-6,7,8,9-tetrahydropyrido[1,2-a]indole (E9)

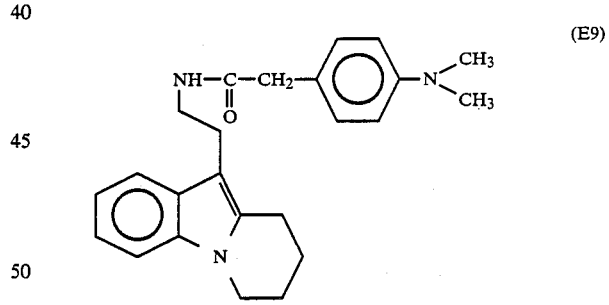

(a) 4-Dimethylaminophenylacetic acid:
23 g 4-Aminophenylacetic acid were dissolved in 250 ml acetonitrile and 160 ml formaldehyde (35% in water) were added.

After cooling to 0° C., 40 g NaBH$_3$CN were added to the mixture, followed by 20 ml acetic acid added dropwise. After stirring for 2 hr at room temperature, again 20 ml acetic acid were added dropwise to the reaction mixture. After 30 minutes it was poured into water and extracted with methylene chloride. The product was dried and the solvent evaporated.

NMR (d$_6$-DMSO) δ=8.99 [1]s; 7.20; 7.09; 6.79; 6.68 [4]-A-B-quartet; 3.53 [2]s; 2.92 [6]s.

(b) The acid chloride of the product of (a) was prepared with SOCl$_2$ according to known methods.

(c) Title Compound 7.2 g E19 of EP-0167901 were dissolved in 100 ml CH$_2$Cl$_2$. After addition of 14.6 ml diisopropylethylamine, 5.15 g 4-dimethylaminophenylacetic acid chloride from (b) in 20 ml CH$_2$Cl$_2$ were added dropwise to the mixture. After 30 minutes the solution was washed with citric acid and with sodium carbonate. The solvent was evaporated and the compound purified by column chromatography (CH$_2$Cl$_2$). The product crystallised from ethyl acetate.

m.p: 141° C.

NMR (CDCl$_3$) δ=7.53–6.47 [8]m; 5.48 [1]s, broad; 3.98 [2]tr,J=6 Hz; 3.45 [4]m; 2.80 [10]m; 1.90 [4]m.

calc.: C 76.77 H 7.78 N 11.19
found: C 77.17 H 7.87 N 11.52.

EXAMPLE 10

10-[2-(4-Dimethylaminobenzoyl)aminoethyl]-6-oxo-6,7,8,9-tetrahydropyrido[1,2-a]indole (E10)

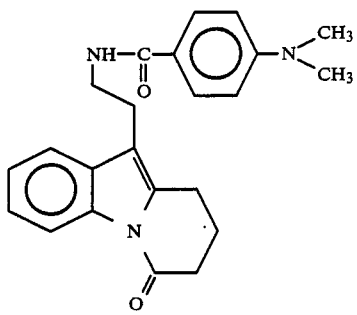

(E10)

E10 was prepared analogously to E9 from 7 g D4 of EP-0167901, 11.2 ml diisopropylethylamine and 4.5 g 4-dimethylaminobenzoic acid chloride.

The product was crystallised from isopropanol/ethyl acetate.

Yield: 6.2 g
m.p: 200° C.

NMR (CDCl$_3$) δ=8.45 [1]m; 7.45 [5]m; 6.62 [2]m; 6.13 [1]m; 3.66 [2]m; 2.80 [12]m; 2.00 [2]m.

calc.: C 73.58 H 6.71 N 11.19
found: C 73.63 H 6.67 N 11.07.

EXAMPLE 11

10-[2-(4-Dimethylaminobenzoyl)aminoethyl]-6,7,8,9-tetrahydropyrido[1,2-a]indole hydrochloride hemihydrate (E11)

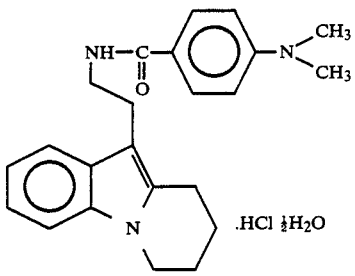

(E11)

5 g E19 of EP-0167901 were dissolved in 100 ml CH$_2$Cl$_2$ and 10 ml diisopropylethylamine were added followed by 4 g 4-dimethylaminobenzoic acid chloride added dropwise. After 2 hours the solution was poured into water, extracted with CH$_2$Cl$_2$ and the organic layer was washed with sodium carbonate. The product was purified by column chromatography (CH$_2$Cl$_2$) and converted to the hydrochloride. The product crystallised from ethyl acetate.

Yield: 1.5 g
m.p: 207° C.

NMR (CDCl$_3$) (+D$_2$O—exchange) δ=7.55 [3]m; 7.20 [3]m; 6.62 [2]m; 4.05 [2]m; 3.67 [2]tr, J=6.5 Hz; 3.00 [10]m; 2.00 [4]m.

EXAMPLE 12

10-[2-(4-Aminobenzylcarbonyl)aminoethyl]-6,7,8,9-tetrahydropyrido[1,2-a]indole hydrochloride hemihydrate (E12)

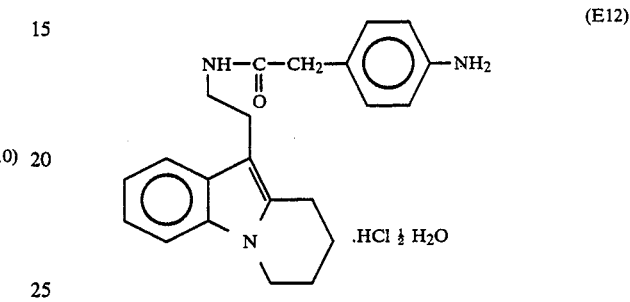

(E12)

6 g E19 of EP-0167901 were dissolved in 100 ml CH$_2$Cl$_2$. 12.2 ml diisopropylethylamine and 4.3 g aminophenylacetic acid chloride were added. The mixture was stirred for 1 hour and was worked up as in Example 11. The obtained hydrochloride crystallised from ethyl acetate.

Yield: 1.3 g
m.p: 254° C.

NMR (d$_6$-DMSO) δ=8.15 [1]m; 7.60–6.80 [8]; 4.00 [2]tr, J=6 Hz; 3.42 [2]s; 3.20 [2]m; 2.75 [4]m; 1.88 [4]m.

EXAMPLE 13

10-[2-(4-Dimethylaminobenzylcarbonyl)aminoethyl]-6-oxo-6,7,8,9-tetrahydropyrido[1,2-a]indole (E13)

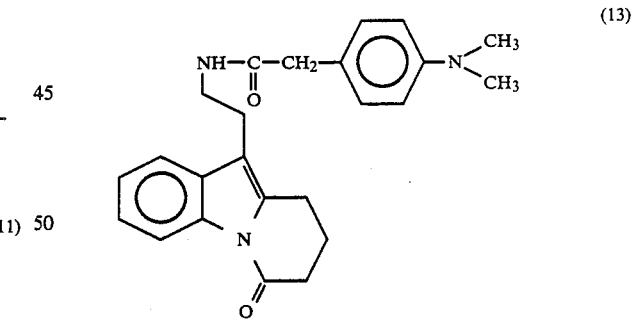

(13)

(a) 11 g 4-Dimethylaminophenylacetic acid (see Example 9a) were dissolved in 100 ml CH$_2$Cl$_2$. Then 10.8 g carbonyldiimidazole were added. After 30 minutes the organic layer was washed with water, dried and evaporated.

Yield: 12.5 g

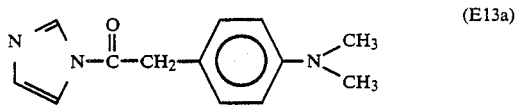

(E13a)

(b) Title compound 15.7 g (0.069 mol) D4 of EP-0167901 and 12.5 g product of Example 13a were dissolved in CH₂Cl₂ and stirred for 3 hours at room temperature. The solvent was evaporated and the product purified by column chromatography (ether/2% CH₃OH). The product crystallised from ethyl acetate.

Yield: 7.4 g
m.p: 146° C.

NMR (CDCl₃) δ=8.45 [1]m; 7.30 [3]m; 6.78 [4], AB-quartet, J=8.8 Hz, J=18 Hz; 3.40 [4]m; 2.93 [6]s; 2.70 [6]tr, J=6.5 Hz; 2.00 [2]m.

EXAMPLE 14

10-[2-(3-Phenylpropionyl)aminoethyl]-6,7,8,9-tetrahydropyrido[1,2-a]-indole (E14)

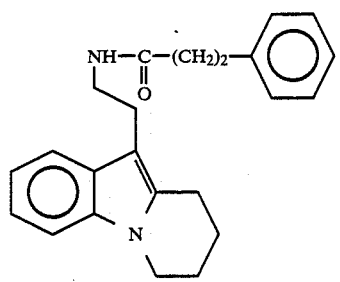

Example 14 was prepared analogously to Example 8 from 15.3 g E19 of EP-0167901, 15.4 ml triethylamine and 12 g 3-phenylpropionic acid chloride.

The product crystallised from ether.
m.p: 99° C.

NMR (DMSO-d₆) δ=7.86 [1]m; 7.21 [9]m; 3.98 [2]tr; 3.20 [2]m; 3.00–2.20 [8]m; 1.90 [4]m.

calc.: C 79.73 H 7.57 N 8.09
found: C 80.16 H 7.62 N 8.02.

EXAMPLE 15

10-[2-(5-[3-Methylpiperidinyl-(1)]-1-oxopentyl)aminoethyl]-6,7,8,9-tetrahydropyrido[1,2-a]indole hydrochloride hemihydrate (E15)

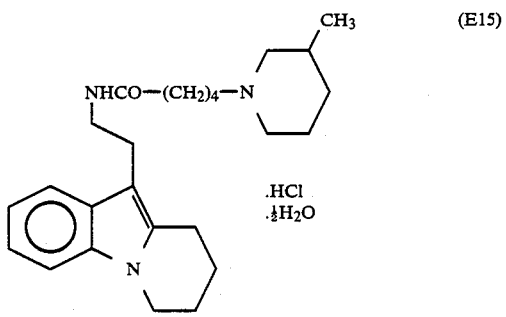

2 g 10-[2-(5-Chlorovaleryl)aminoethyl]-6,7,8,9-tetrahydropyrido[1,2-a]indole (D6 of EP-0213696), 1.2 g 3-methylpiperidine and 0.2 g KI in 20 ml DMF were heated at 55° C. for 14 hours.

The reaction mixture was then diluted with 200 ml water and extracted with ethyl acetate. After acid/base separation with citric acid/sodium carbonate, the crude product was converted into the hydrochloride and crystallized from isopropanol/diisopropylether.

m.p: 118° C. (dec.)

NMR (d₆-DMSO) δ=10.65 [1]s, broad; 8.00 [1]s, broad; 7.55–6.85 (4)m; 4.00 [2]tr, J=5.5 Hz; 3.55–2.55 [11]m; 2.30–1.30 [16]m; 0.85 [3]d, J=6 Hz.

EXAMPLE 16

10-[2-(6-[N,N-Dimethylamino]-1-oxohexyl)aminoethyl]-6-oxo-6,7,8,9-tetrahydropyrido[1,2-a]indole (E16)

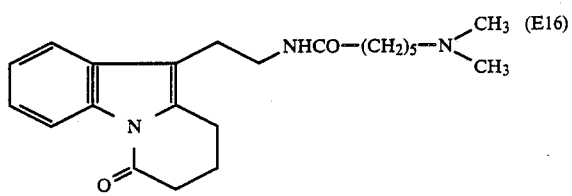

8.9 g (0.022 mole) D4, 3.2 g (0.44 mole) dimethylammonium chloride and 6 g triethylamine were dissolved in 150 ml N,N-dimethylformamide and heated for 6 h at 90° C. The solvent was evaporated in vacuo and the residue extracted with 100 ml chloroform and 100 ml water. The organic layer was separated and dried. The solvent was evaporated and the residue crystallised from ethyl acetate.

Yield: 0.7 g
m.p: 103° C.

EXAMPLE 17

10-[2-(6-[3,5-Dimethylpiperidinyl-(1)]-1-oxohexyl)-aminoethyl]-6-oxo-6,7,8,9-tetrahydropyrido[1,2-a]indole hydrochloride (E17)

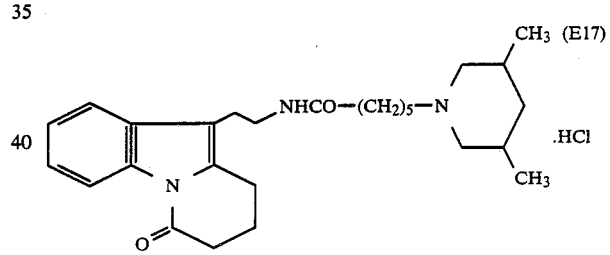

4.05 g (0.01 mole) D4, 1.7 g (0.015 mole) 3,5-dimethylpiperidine and 1.5 g (0.015 mole) triethylamine were dissolved in 50 ml DMF and heated under stirring at 75° C. for 2 h.

The solvent was evaporated and the residue was taken up in water/methylene chloride (150 ml/150 ml). The layers were separated. The organic layer was extracted with Na₂CO₃ solution and dried. The solvent was evaporated in vacuo and the residue purified by column chromatography over silica gel (CH₂Cl₂) and crystallized from ethyl acetate.

Yield: 2.2 g (50%)
m.p: 120°–121° C.
calc.: C 74.14 H 8.92 N 9.61
found: C 73.94 H 8.85 N 9.49.

The base was converted to the hydrochloride salt by the addition of an equivalent amount of isopropanolic solution of HCl (0.1 N).

The product was crystallized from ethyl acetate.
Yield: 2.1 g
m.p: 157°–158° C. (decomp.).

EXAMPLE 18

10-[2-(4-[2,4-Dimethylpyrrolidinyl-(1)]-1-oxobutyl)aminoethyl]-6,7,8,9-tetrahydropyrido[1,2-a]indole(E18)

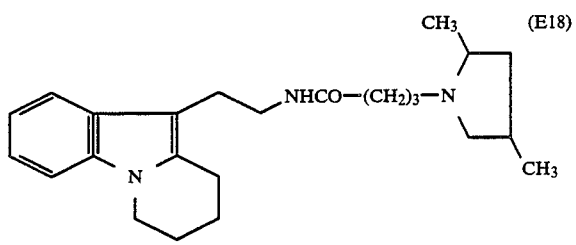

2.2 g (0.007 mole) D6 and 3.1 g (0.028 mole) 2,4-dimethylpyrrolidine were heated to 60°-70° C. for 3 hours. The reaction mixture was thereafter diluted with 100 ml ethyl acetate and extracted with water and a solution of citric acid. The layers were separated. The aqueous phase was made alkaline with $Na_2CO_3$ and extracted with ethyl acetate. The organic layer was separated, dried and evaporated. The residue was purified by column chromatography ($SiO_2/CH_2Cl_2$).

Yield: 1.4 g (52%) oily product.
calc.: C 75.59 H 9.19 N 11.02
found: C 75.53 H 9.20 N 11.40

The compounds of Examples 19 and 20 were prepared by an analogous procedure to that of Example 18.

EXAMPLE 19

10-[2-(4-[2-Methylpiperidinyl-(1)]-1-oxobutyl)aminoethyl]-6,7,8,9-tetrahydropyrido[1,2-a]indole (E19)

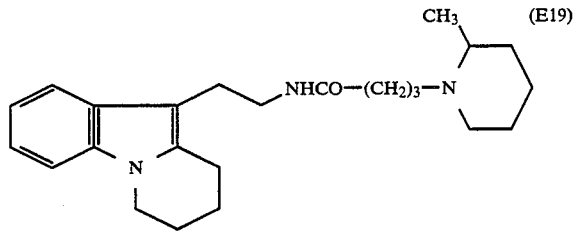

EXAMPLE 20

10-[2-(4-[Morpholinyl-(1)]-1-oxobutyl)aminoethyl]-6,7,8,9-tetrahydropyrido[1,2-a]indole (E20)

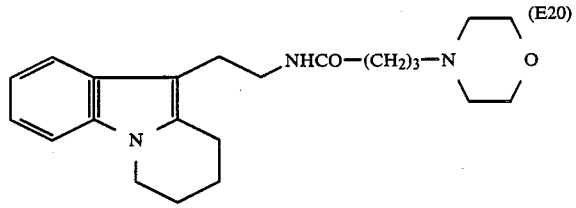

Yield: 43%
m.p: 94° C.
calc.: C 71.5 H 8.40 N 11.38
found: C 71.4 H 8.40 N 11.85
Hydrochloride
m.p: 177°-179° C.

EXAMPLE 21

10-[2-(6-[N,N-Dimethylamino]-1-oxohexyl)aminoethyl]-6,7,8,9-tetrahydropyrido[1,2-a]indole hydrochloride hydrate (E21)

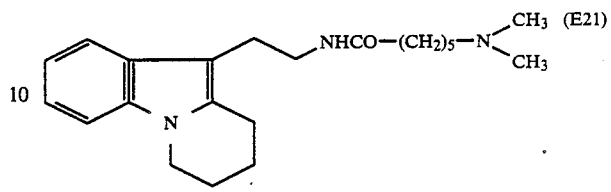

5.9 g (0.015 mole) D5, 2.4 g (0.03 mole) dimethylamine hydrochloride and 1.2 g (0.03 mole) NaOH were dissolved in 80 ml DMF and 3 ml water. The reaction mixture was heated to 75° C. for 2 hours. The solvent was evaporated and the residue purified by column chromatography on silica gel ($CH_2Cl_2$).

Yield: 2.5 g (33.5%)

The compound was converted to the hydrochloride and crystallised from ethyl acetate/ethyl alcohol.
Yield: 1.7 g
m.p: 116°-118° C.
calc.: C 64.47 H 8.79 N 10.26 Cl 8.67
found: C 64.88 H 8.47 N 9.94 Cl 8.39.

The compounds of Examples 22 to 25 were prepared by an analogous procedure to that of Example 21.

EXAMPLE 22

10-[2-(6-[3,5-Dimethylpiperidinyl-(1)]-1-oxohexyl)aminoethyl]-6,7,8,9-tetrahydropyrido[1,2-a]indole (E22)

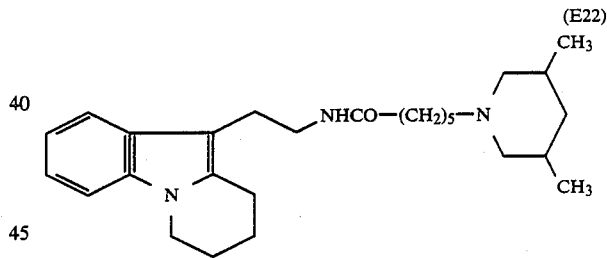

Yield: 69%
m.p: 88°-90° C.
calc.: C 76.60 H 9.69 N 9.93
found: C 76.55 H 9.67 N 9.87.

EXAMPLE 23

10-[2-(6-[2,6-Dimethylpiperidinyl-(1)]-1-oxohexyl)aminoethyl]-6,7,8,9-tetrahydropyrido[1,2-a]indole (E23)

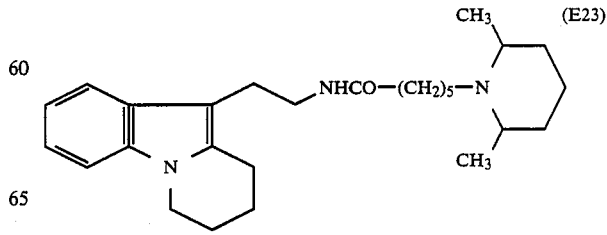

Yield: 26% calc.: C 76.60 H 9.69 N 9.93
found: C 76.50 H 8.70 N 9.88.

EXAMPLE 24

10-[2-(6-[3-Methylpiperidinyl-(1)]-1-oxohexyl)aminoethyl]-6,7,8,9-tetrahydropyrido[1,2-a]indole (E24)

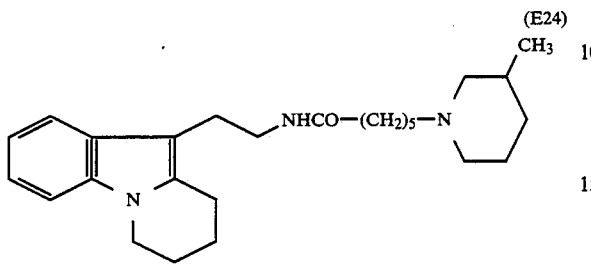
(E24)

Yield: 75%
m.p: 99°–100° C.
calc.: C 76.28 H 9.54 N 10.27
found: C 76.28 H 9.57 N 10.21.

EXAMPLE 25

10-[2-(6-Piperidinyl-(1)-1-oxohexyl)aminoethyl]-6,7,8,9-tetrahydropyrido[1,2-a]indole hydrochloride hydrate (E25)

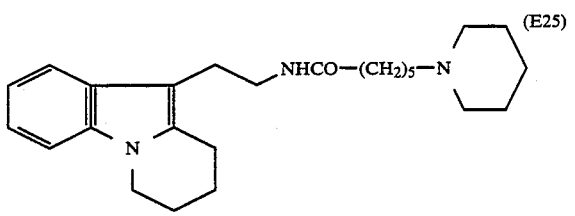
(E25)

Yield: 70%
m.p: 160–165%
calc.: C 66.74 H 9.90 N 9.34 Cl 7.90
found: C 65.74 H 8.63 N 9.22 Cl 8.42.

EXAMPLE 26

10-[2-(3-[3,5-Dimethylpiperidinyl-(1)]-1-oxopropyl)aminoethyl]-6,7,8,9-tetrahydropyrido[1,2-a]indole (E26)

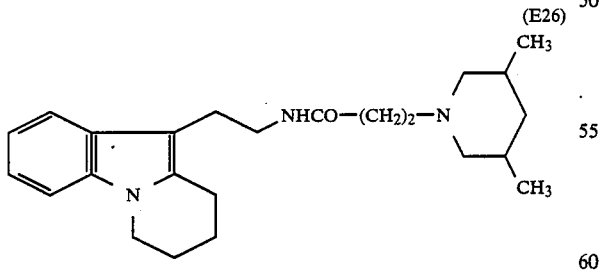
(E26)

Compound E26 was prepared from intermediate D7 and 3,5-dimethylpiperidine by an analogous procedure to that of Example 21.
m.p: 136° C.
calc.: C 75.55 H 9.25 N 11.01 O 4.19
found: C 75.43 H 9.23 N 10.92 O 4.18
Hydrogensulphate m.p: 208° C.

EXAMPLE 27

10-[2-(2-[3,5-Dimethylpiperidinyl-(1)]-1-oxoethyl)aminoethyl]-6,7,8,9-tetrahydropyrido[1,2-a]indole (E27)

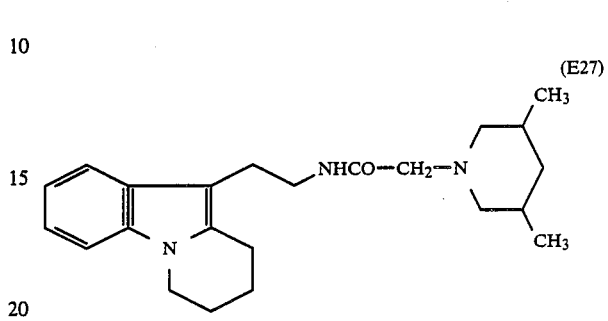
(E27)

Compound E27 was prepared from intermediate D8 and 3,5-dimethylpiperidine by an analogous procedure to that of Example 21.
Yield: 67%, oil
calc.: C 72.51 H 9.05 N 11.43 O 4.35
found: C 72.88 H 8.88 N 10.98 O 6.63
NMR (CDCl$_3$) δ=8.2 [1]s broad (exch.); 7.4–7.6 [1]m;
6.9–7.3[3]m; 3.9–4.1 [2]t; 3.3–3.7 [2]q; 2.8–3.0 [4]t; 0.9–2.7 [16]m; 0.7–0.8 [6]d.

EXAMPLE 28

10-[2-(4-[2,5-Dimethylpyrrolidyl-(1)]-1-oxobutyl)aminoethyl]-6,7,8,9-tetrahydropyrido[1,2-a]indole (E28)

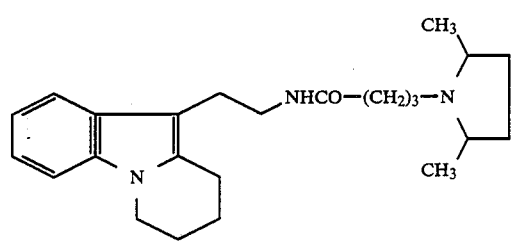

The compound E28 was prepared from intermediate D6 and 2,5-dimethylpyrrolidine by an analogous procedure to that of Example 18. Yield 55% of theory. The compound was converted to hydrochloride which is amorphous and hygroscopic.
calc.: C 66.13 H 8.73 N 9.64 Cl 8.15
found: C 66.04 H 8.66 N 9.40 Cl 7.92

EXAMPLE 29

10-[2-(4-[3,5-Dimethylpiperidinyl-(1)]-1-oxobutyl)-N-methylaminoethyl]-6,7,8,9-tetrahydropyrido[1,2-a]indole (E29)

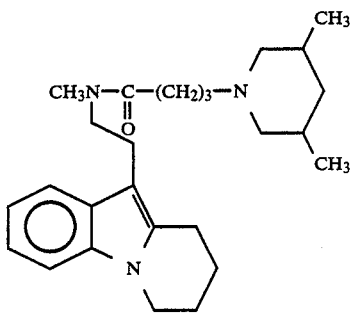

1.9 g D10 and 2.6 g 3,5-dimethylpiperidine was heated for 2 hours at 70° C. The reaction mixture was taken up in ethyl acetate and shaken with water and citric acid solution. The water phase was made alkaline with sodium carbonate solution and extracted with ethyl acetate. The organic extract was dried and evaporated yielding 1.4 g (60% of theory) oily E29 base.

calc.: C 76.28 H 9.54 N 10.27
found: C 75.05 H 9.59 N 10.44

EXAMPLE 30

10-[2-(4-[2,4-Dimethylpyrrolidinyl-(1)]-1-oxobutyl)-N-methylaminoethyl]-6,7,8,9-tetrahydropyrido[1,2-a]indole (E30)

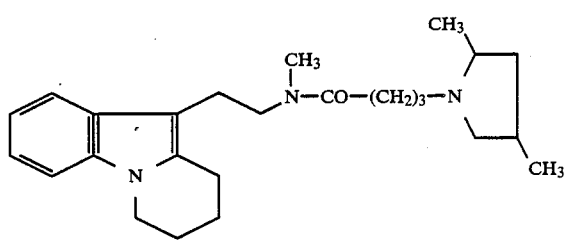

The compound E 30 was prepared from intermediate D10 and 2,4-dimethylpyrrolidine by an analogous procedure to that of Example 29. Yield 44% of theory.
calc.: C 75.94 H 9.37 N 10.63
found: C 75.79 H 9.16 N 10.65

EXAMPLE 31

10-[2-(3-Phenylpropionyl)aminoethyl]-6-oxo-6,7,8,9-tetrahydropyrido[1,2-a]indole (E31)

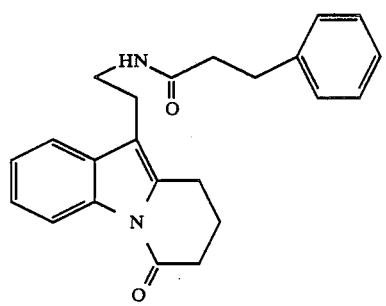

10.6 g (409mM) D 4 (EP 0167901) HCl were suspended in 200 ml $CH_2Cl_2$ and, at 0° C., 10 ml 3-phenylpropionylchloride were added. Thereafter, the mixture was cooled to $-20°$ C. and 20 ml diisopropylethylamine were added dropwise. The mixture was allowed to warm to room temperature and shaken three times, each with a 10% solution of citric acid and sodium carbonate. The organic phase was dried with $Na_2SO_4$, filtered and evaporated. The residue was heated with charcoal in 400 ml methanol and concentrated to about 150 ml and, after cooling, 10.8 g of white crystals were obtained.

m.p: 109° C.

NMR ($CDCl_3$) $\delta = 1.8$–$2.2$ [2]m; $2.3$–$2.6$ [2]m; $2.6$–$3.1$ [8] m; 3.39 [2] q J=7 Hz (after exchange tr.); 5.55 [1] s broad, exchange; 7.0–7.6 [8] m; 8.4–8.6 [1] m.

Pharmacological Data

1. Triethyltin-induced cerebral oedema in the rat.

The cerebral oedema is induced by oral administrations repeated for 5 consecutive days—one administration per day—of triethyltin chloride at a dose of 2 mg/kg. The study substances are also administered orally twice daily as aqueous solution or suspension at a dose of 1 ml/100 g body-weight; these administrations are given during the 5 days of intoxication with tin. Three groups of 10 male specific pathogen-free (SPF) Wistar rats of 280±10 g body-weight are used for each compound studied:

1 control group
1 group intoxicated with triethyltin
1 group intoxicated with triethyltin and treated with the studied compound.

The rats are killed on the evening of the fifth day; the brain is removed, weighed fresh and after desiccation to constant weight and the water content of each brain is calculated:

[$H_2O$] = fresh weight − dry weight.

The following are then calculated:
the mean water content (M±Sm %) of each group;
the protection index P due to the administered compound:

$$P\% = 1 - \frac{[H_2O] \text{ treated group} - [H_2O] \text{ control group}}{[H_2O] \text{ triethyltin group} - [H_2O] \text{ control group}} \times 100$$

The results are shown in Table 1.

TABLE 1

| Compound No. | Triethyltin-induced cerebral oedema % protection at dose administered (mg/kg p.o.) | | | |
|---|---|---|---|---|
| | 2 × 5 | 2 × 12.5 | 2 × 25 | Significance |
| E7 | | 65 | | b |
| E8 | | 50 | | c |
| E9 | 77 | 95 | | a |
| E10 | | 35.5 | | c |
| E17 | | | 47.3 | b |
| E18 | | | 41.4 | c |

Significance:
a: $p < 0.01$
b: $p < 0.05$
c: $p = 0.05$

2. The Gerbil Ischaemic Deficit Passive Avoidance Test.

Mongolian gerbils were conditioned to avoid entering a dark compartment by means of a footshock (maximally 50 V, 2 s duration) received when entering from the light section of a two compartment box. Recollection of the footshock was examined 24 h later by replacing the gerbils in the two compartment box and measuring the recall latency, the time taken to re-enter the dark compartment.

Effect of test compound on recall latency in the gerbil following transient forebrain ischaemia.

(a) Animal Preparation

A learning or memory deficit was induced in the gerbils by a transient (5 min) bilateral carotid artery ligation, performed 24 h prior to conditioning, under light hexobarbital anaesthesia.

(b) Measurement

Compounds, being examined for an effect on learning or memory in gerbils which had undergone carotid occlusion, were administered seven times during the experiment. The initial administration was during the period of forebrain ischaemia, the third and seventh administrations were 10 min prior to conditioning and recall testing, respectively, and the remainder were given at intermediate time points.

Results were expressed as percentage of animals which had a long recall latency (>60 s). A long recall latency indicates good information acquisition or retrieval.

(c) Results

The results for test compounds are shown in Table 2.

TABLE 2

| | Percentage of animals with recall latencies >60s | | |
|---|---|---|---|
| I | sham-ligated controls | 33 | |
| II | Ischaemic controls | 14 | |
| III | Ischaemia and test compound | | |
| | No. Dose (mg/kg) | | |
| | E4 | 50 p.o. | 46 (d) |
| | E7 | 50 p.o. | 28 (d) |
| | E8 | 12.5 p.o. | 44 (c) |
| | E10 | 12.5 p.o. | 39 (b) |
| | | 50 p.o. | 57 (d) |
| | E18 | 12.5 s.c. | 73 (a) |
| | E26 | 12.5 s.c. | 36 (c) |
| | E27 | 5 s.c. | 31 (c) |
| | E29 | 12.5 s.c. | 46 (d) |

III significantly different from II:
a: $p < 0.001$
b: $p < 0.01$
c: $p < 0.02$
d: $p < 0.05$ As can be seen in Table 2, transient cerebral ischaemia impairs the recollection of the footstock in gerbils. The test compounds significantly increased the percentage of animals with long recall latencies.

The above results show that the test compounds improve data acquisition or retrieval in the gerbil following transient forebrain ischaemia and demonstrate that the compounds of the invention are of potential use in the treatment of cerebral vascular and neuronal degenerative disorders associated with learning, memory and cognitive dysfunctions including cerebral senility, multi-infarct dementia and senile dementia of the Alzheimer type.

We claim:

1. A compound of formula (I) or a pharmaceutically acceptable salt thereof

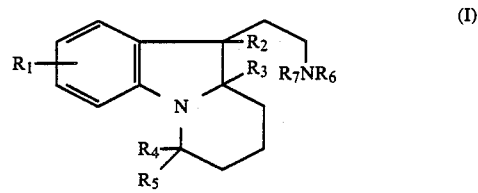

wherein $R_1$ is hydrogen, alkyl of 1 to 6 carbon atoms, alkoxy of 1 to 6 carbon atoms or halogen;

$R_2$ and $R_3$ are both hydrogen or together represent a bond;

$R_4$ and $R_5$ are each hydrogen or $R_4$ and $R_5$ together represent an oxo group;

$R_6$ is phenyl alkanoyl of 1 to 7 carbon atoms in the alkanoyl moiety unsubstituted or substituted in the phenyl moiety by one or two members selected from the group consisting of halogen, nitro, meta-methoxy, para-methoxy, methyl and $NR_8R_9$, wherein $R_8$ and $R_9$ are independently hydrogen or alkyl of 1 to 6 carbon atoms, or $R_8$ and $R_9$ together are polymethylene of 2 to 6 carbon atoms, or said phenyl moiety is 3,4-disubstituted by methylenedioxy or ethylenedioxy; or alkanoyl of 1 to 7 carbon atoms substituted by $NR_{10}R_{11}$, wherein $R_{10}$ and $R_{11}$ are independently hydrogen or alkyl of 1 to 4 carbon atoms or together are polymethylene of 3 to 7 carbon atoms optionally containing a further hetereoatom which is oxygen, sulphur or nitrogen substituted by $R_{12}$ wherein $R_{12}$ is hydrogen, alkyl of 1 to 4 carbon atoms or benzyl unsubstituted or substituted by one or two members selected from the group consisting of alkyl of 1 to 4 carbon atoms, alkanoyl of 2 to 5 carbon atoms, alkoxycarbonyl of 1 to 4 carbon atoms, aminocarbonyl unsubstituted or mono-or di- substituted by alkyl of 1 to 6 carbon atoms or by cyano, phenyl or benzyl wherein any phenyl or benzyl is unsubstituted or substituted in the phenyl ring by one or two members selected from the group consisting of halo, $CF_3$, alkyl of 1 to 4 carbon atoms, alkoxy of 1 to 4 carbon atoms, cyano and nitro; and $R_7$ is hydrogen or alkyl of 1 to 4 carbon atoms, provided however that said compound is not 6-oxo-10-[2-(3-nitrobenzoyl)aminoethyl]-6,7,8,9-tetrahydropyrido[1,2-a]indole, 6-oxo-10-[2-(3-aminobenzoyl)aminoethyl]-6,7,8,9-tetrahydropyrido[1,2-a]indole, 6-oxo-10-[2-(5-[3,5-dimethyl-piperidyl-(1)]valeryl) aminoethyl]-6,7,8,9-tetrahydropyrido[1,2-a]indole, 10-[2-(5-[3,5-dimethyl-piperidyl-(1)]valeryl) aminoethyl]-6,7,8,9-tetrahydropyrido[1,2-a]indole, 10-[2-(5-dimethylaminovaleryl)aminoethyl]-6,7,8,9-tetrahydropyrido[1,2-a]indole, 10-[2-(5-[piperidyl-(1)]valeryl)aminoethyl]-6,7,8,9-tetrahydropyrido[1,2-a]indole, 10-[2-(5-[pyrrolidinyl-(1)]valeryl)aminoethyl]-6,7,8,9-tetrahydropyrido[1,2-a]indole, 10-[2-(5-[morpholinyl-(1)]valeryl)aminoethyl]-6,7,8,9-tetrahydropyrido[1,2a]indole, 6-oxo-10-[2-(3-piperidinobenzoyl)aminoethyl]-6,7,8,9-tetrahydropyrido[1,2-a]indole,
6-oxo-10-[2-(3-diisopropylaminobenzoyl)aminoethyl]-6,7, 8,9-tetrahydropyrido[1,2-a]indole,
6-oxo-10-[2-(3-pyrrolidinobenzoyl)aminoethyl]-6,7,8,9-tetrahydropyrido[1,2-a]indole,
6-oxo-[2-benzoylaminoethyl]-6,7,8,9,-tetrahydropyrido[1,2-a]indole,
6-oxo-10-[2-(3-dimethylaminobenzoyl)aminoethyl]-6,7,8,9-tetrahydropyrido[1,2-a]indole,
2-methyl-6-oxo-10-[2-benzoylaminoethyl]-6,7,8,9-tetrahydropyrido [1,2-a]indole,
10-[2-(4-nitrobenzoyl)aminoethyl[-6,7,8,9-tetrahydropyrido[1,2-a]indole or
10-[2-(4-aminobenzoyl)aminoethyl]-6,7,8,9-tetrahydropyrido[1 2-a]indole.

2. A compound selected from the group consisting of
10-[2-(4-Chloro-1-oxobutyl)aminoethyl]-6-oxo-6,-7,8,9-tetrahydropyrido[1,2-a]indole
10-[2-(6Bromo-1-oxohexyl)aminoethyl]-6-oxo-6,7,8, 9-tetrahydropyrido[1,2,-a]indole
10-[2-(6-Bromo-1-oxohexyl)aminoethyl]-6,7,8, 9-tetrahydropyrido[1,2,-a]indole
10-[2-(4-Chloro-1-oxobutyl)aminoethyl]-6,7,8,9-tetrahydropyrido[1,2,-a]indole
10-[2-(3-Chloro-1-oxopropyl)aminoethyl-6,7,8,9-tetrahydropyrido[1,2-a]indole
10-[2-(2-Chloro-1-oxoethyl)aminoethyl]-6,7,8,9-tetrahydropyrido[1,2-a]indole, and
10-[2-(4-Chloro-1-oxobutyl-N-methylaminoethyl]-6,7,8,9-tetrahydropyrido[1,2-a]indole.

3. 10-[2-(3-Nitrobenzoyl)aminoethyl]-6,7,8,9-tetrahydropyrido[1,2-a]indole,
10-[2-(3-aminobenzoyl)aminoethyl]-6,7,8,9-tetrahydropyrido[1,2-a]indole,
10-[2-(5-dimethylamino-1-oxopentyl)aminoethyl]-6-oxo-6,7,8,9-tetrahydropyrido[1,2-a]indole,
10-[2-(5-piperidinyl-(1)-1-oxopentyl)aminoethyl]-6-oxo-6,7,8,9-tetrahydropyrido[1,2-a]indole,
10-[2-(5-[3-methylpiperidinyl-(1)]-1-oxopentyl) aminoethyl]-6-oxo-6,7,8,9-tetrahydropyrido[1,2-a]indole,
10-[2-(4-[3,5-dimethylpiperidinyl-(1)]-1-oxo-butyl)aminoethyl]-6-oxo-6,7,8, 9-tetrahydropyrido [1,2-a]indole,
10-[2-(4-[3,5-dimethylpiperidinyl-(1)]-1-oxobutyl)-aminoethyl]-6,7,8, 9-tetrahydropyrido[1,2-a]indole,
10-[2-(2-phenylacetyl)aminoethyl]-6,7,8,9-tetrahydropyrido[1,2-a]indole,
10-[2-(4-dimethylaminobenzylcarbonyl)aminoethyl]-6,7,8,9-tetrahydropyrido[1,2-a]indole,
10-[2-(4-dimethylaminobenzoyl)aminoethyl]-6-oxo-6,7,8,9-tetrahydropyrido[1,2-a]indole,
10-[2-(4-dimethylaminobenzoyl)aminoethyl]-6,7,8,9-tetrahydropyrido[1,2-a]indole,
10-[2-(4-aminobenzylcarbonyl)aminoethyl]-6,7,8,9-tetrahydropyrido[1,2-a]indole,
10-[2-(4-dimethylaminobenzylcarbonyl)aminoethyl]-6-oxo-6,7,8,9-tetrahydropyrido[1,2-a]indole,
10-[2-(3-phenylpropionyl)aminoethyl]-6,7,8,9-tetrahydropyrido[1,2-a]-indole,
10-[2-(5-[3-methylpiperidinyl-(1)-1-oxopentyl)aminoethyl]-6,7,8,9-tetrahydropyrido[1,2-a]indole,
10-[2-(6-[N,N-dimethylamino]-1-oxohexyl)aminoethyl]-6-oxo-6,7,8, 9-tetrahydropyrido[1,2-a]indole,
10-[2-(6-[3,5-dimethylpiperidinyl-(1)]-1-oxohexyl)-aminoethyl]-6-oxo-6,7,8, 9-tetrahydropyrido[1,2-a]indole,
10-[2-(4-[2,4-dimethylpyrrolidinyl-(1)]-1-oxobutyl) aminoethyl]-6,7,8,9-tetrahydropyrido[1,2-a]indole,
10-[2-(4-[2-methylpiperidinyl-(1)-1oxobutyl) aminoethyl]-6,7,8,9-tetrahydropyrido[1,2-a]indole,
10-[2-(4-[morpholinyl-(1)]-1-oxobutyl)aminoethyl]-6,7,8, 9-tetrahydropyrido[1,2-a]indole,
10-[2-(6-[N,N-dimethylamino]-1-oxohexyl)aminoethyl]-6,7,8,9-tetrahydropyrido[1,2-a]indole,
10-[2-(6-[3,5-dimethylpiperidinyl-(10]-1-oxohexyl) aminoethyl]-6,7,8,9-tetrahydropyrido[1,2-a]indole,
10-[2-(6-[2,6-dimethylpiperidinyl-(1)]-1-oxohexyl) aminoethyl]-6,7,8,9-tetrahydropyrido[1,2-a]indole,
10-[2-(6-[3-methylpiperidinyl-(1)]-1-oxohexyl) aminoethyl]-6,7,8,9-tetrahydropyrido[1,2-a]indole,
10-[2-(6-piperidinyl-(1)-1-oxohexyl)aminoethyl]-6,7,8,9-tetrahydropyrido[1,2-a]indole,
10-[2-(3-[3,5-dimethylpiperidinyl-(1)]-1-oxopropyl) aminoethyl]-6,7,8,9-tetrahydropyrido[1,2-a]indole,
10-[2-(2-[3,5-dimethylpiperidinyl-(1)-1-oxoethyl)amino ethyl]-6,7,8,9-tetrahydropyrido[1,2-a]indole,
10-[2-(4-[2,5-dimethylpyrrolidyl-(1)-1-oxobutyl) aminoethyl]-6,7,8,9-tetrahydropyrido[1,2-a]indole,
10-[2-(4-[3,5-dimethylpiperidinyl-(1)]-oxobutyl)-N-methylaminoethyl]-6,7,8, 9-tetrahydropyrido[1,2-a]indole,
10-[2-(4-[2,4-dimethylpyrrolidinyl-(1)]-1-oxobutyl)-N-methylaminoethyl]-6,7,8, 9-tetrahydropyrido[1,2-a]indole or
10-[2-(3-phenylpropionyl)aminoethyl]-6-oxo-6,7,8,9-tetrahydropyrido[1,2-a]indole.

4. A pharmaceutical composition useful for the treatment of cerebral vascular and neuronal degenerative disorders, which comprises a therapeutically effective amount of a compound of formula (I) or a pharmaceutically acceptable salt thereof:

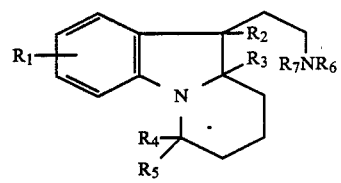

wherein:
$R_1$ is hydrogen, alkyl of 1 to 6 carbon atoms, alkoxy of 1 to 6 carbon atoms or halogen;
$R_2$ and $R_3$ are both hydrogen or together represent a bond;
$R_4$ and $R_5$ are each hydrogen or $R_4$ and $R_5$ together represent an oxo group;
$R_6$ is phenyl alkanoyl of 1 to 7 carbon atoms in the alkanoyl moiety unsubstituted or substituted in the phenyl moiety by one or two members selected from the group consisting of halogen, nitro, meta-methoxy, para-methoxy, methyl and $NR_8R_9$, wherein $R_8$ and $R_9$ are independently hydrogen or alkyl of 1 to 6 carbon atoms or $R_8$ and $R_9$ together are polymethylene of 2 to 6 carbon atoms, or said phenyl moiety is 3,4-disubstituted by methylenedioxy or ethylenedioxy; or alkanoyl of 1 to 7 carbon atoms substituted by $NR_{10}R_{11}$, wherein $R_{10}$ and $R_{11}$ are independently hydrogen or alkyl of 1 to 4 carbon atoms or together are polymethylene of 3 to 7 carbon atoms optionally containing a further hetereoatom which is a member selected from the group consisting of oxygen, sulphur and nitrogen substituted by $R_{12}$ wherein $R_{12}$ is hydrogen, alkyl of 1 to 4 carbon atoms or benzyl, unsubstituted or substituted by one or two members selected from the group consisting of alkyl of 1 to 4 carbon atoms, alkanoyl of 2 to 5 carbon atoms, alkoxycarbonyl of 1 to 4 carbon atoms, aminocarbonyl unsubstituted or mono-or di- substituted by alkyl of 1 to 6 carbon atoms or by cyano, phenyl or benzyl wherein any phenyl or benzyl is unsubstituted or substituted in the phenyl ring by one or two members selected from the group consisting of halo, $CF_3$, alkyl of 1 to 4 carbon atoms, alkoxy of 1 to 4 carbon atoms, cyano and nitro; and $R_7$ is hydrogen or alkyl of 1 to 4 carbon atoms; in combination with a pharmaceutically acceptable carrier.

5. A pharmaceutical composition according to claim 4, wherein $R_1$ is hydrogen and $R_2$ and $R_3$ is a bond.

6. A pharmaceutical composition according to claim 4, wherein $R_4$ and $R_5$ are each hydrogen.

7. A pharmaceutical composition according to claim 4, wherein $R_7$ is hydrogen.

8. A pharmaceutical composition according to claim 4, wherein $R_6$ is benzoyl, 1-methyl-2-phenylacetyl unsubstituted or monosubstituted in the phenyl moiety by $NR_8R_9$, or alkanoyl of 3 to 7 carbon atoms substituted by $NR_{10}R_{11}$.

9. A pharmaceutical composition according to claim 8 wherein $R_{10}$ and $R_{11}$ together are polymethylene of 3 to 7 carbon atoms optionally containing a further heteroatom which is a member selected from the group consisting of oxygen, sulphur and nitrogen substituted by $R_{12}$ where $R_{12}$ is hydrogen, alkyl of 1 4 carbon atoms or benzyl unsubstituted or mono- or di-substituted by alkyl of 1 to 4 carbon atoms.

10. A pharmaceutical composition according to claim 9, wherein $NR_{10}R_{11}$ comprises 5 to 7 ring atoms.

11. A pharmaceutical composition according to claim 10, wherein $NR_{10}R_{11}$ is a member selected from the group consisting of 1-piperidyl, 2-methyl-1-piperidyl, 3-methyl-1-piperidyl, 3,5-dimethyl-1-piperidyl, 2,6-dimethyl-1-piperidyl, 2,5-dimethyl-1-pyrrolidyl, 2,4-dimethyl-1-pyrrolidyl and 1-morpholinyl.

12. A pharmaceutical composition according to claim 8, wherein $R_6$ is alkanoyl of 3 to 5 carbon atoms substituted by $NR_{10}R_{11}$.

13. A method of treating cerebral vascular and neuronal degenerative disorders in mammals, which comprises administering to a mammal in need thereof a therapeutically effective amount of a compound of formula (I) or a pharmaceutically acceptable salt thereof

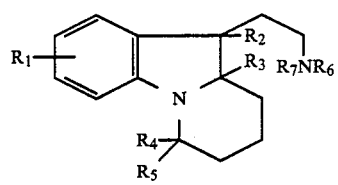

(I)

wherein $R_1$ is hydrogen, alkyl of 1 to 6 carbon atoms, alkoxy of 1 to 6 carbon atoms or halogen;

$R_2$ and $R_3$ are both hydrogen or together represent a bond;

$R_4$ and $R_5$ are each hydrogen or $R_4$ and $R_5$ together represent an oxo group;

$R_6$ is phenyl alkanoyl of 1 to 7 carbon atoms in the alkanoyl moiety unsubstituted or substituted in the phenyl moiety by one or two members selected from the group consisting of halogen, nitro, meta-methoxy, para-methoxy, methyl and $NR_8R_9$, wherein $R_8$ and $R_9$ are independently hydrogen or alkyl of 1 to 6 carbon atoms, or $R_8$ and $R_9$ together are polymethylene of 2 to 6 carbon atoms, or said phenyl moiety is 3,4-disubstituted by methylenedioxy or ethylenedioxy; or alkanoyl of 1 to 7 carbon atoms substituted by $NR_{10}R_{11}$, wherein $R_{10}$ and $R_{11}$ are independently hydrogen or alkyl of 1 to 4 carbon atoms or together are polymethylene of 3 to 7 carbon atoms optionally containing a further hetereoatom which is oxygen, sulphur or nitrogen substituted by $R_{12}$ wherein $R_{12}$ is hydrogen, alkyl of 1 to 4 carbon atoms or benzyl unsubstituted or substituted by one or two members selected from the group consisting of alkyl of 1 to 4 carbon atoms, alkanoyl of 2 to 5 carbon atoms, alkoxycarbonyl of 1 to 4 carbon atoms, aminocarbonyl unsubstituted or mono-or di- substituted by alkyl of 1 to 6 carbon atoms or by cyano, phenyl or benzyl wherein any phenyl or benzyl is unsubstituted or substituted in the phenyl ring by one or two members selected from the group consisting of halo, $CF_3$, alkyl of 1 to 4 carbon atoms, alkoxy of 1 to 4 carbon atoms, cyano and nitro; and $R_7$ is hydrogen or alkyl of 1 to 4 carbon atoms,
in combination with a pharmaceutically acceptable carrier.

14. A method according to claim 13, wherein $R_1$ is hydrogen and $R_2$ and $R_3$ is a bond.

15. A method according to claim 13, wherein $R_4$ and $R_5$ are each hydrogen.

16. A method according to claim 13, wherein $R_7$ is hydrogen.

17. A method according to claim 13, wherein $R_6$ is benzoyl, 1-methyl-2-phenylacetyl unsubstituted or monosubstituted in the phenyl moiety by $NR_8R_9$, or alkanoyl of 3 to 7 carbon atoms substituted by $NR_{10}R_{11}$.

18. A method according to claim 17, wherein $R_{10}$ and $R_{11}$ together are polymethylene of 3 to 7 carbon atoms optionally containing a further heteroatom which is a member selected from the group consisting of oxygen, sulphur and nitrogen substituted by $R_{12}$ where $R_{12}$ is hydrogen, alkyl of 1 to 4 carbon atoms or benzyl unsubstituted or mono or di-substituted by alkyl of 1 to 4 carbon atoms.

19. A method according to claim 18, wherein $NR_{10}R_{11}$ comprises 5 to 7 ring atoms.

20. A method according to claim 19, wherein $NR_{10}R_{11}$ is a member selected from the group consisting of 1-piperidyl, 2-methyl-1-piperidyl, 3-methyl-1-piperidyl, 3,5-dimethyl-1-piperidyl, 2,6-dimethyl-1-piperidyl, 2,5-dimethyl-1-pyrrolidyl, 2,4-dimethyl-1-pyrrolidyl and 1-morpholinyl.

21. A method according to claim 17, wherein $R_6$ is alkanoyl of 3 to 5 carbon atoms substituted by $NR_{10}R_{11}$.

* * * * *